United States Patent
Nelson et al.

(10) Patent No.: US 7,906,288 B2
(45) Date of Patent: Mar. 15, 2011

(54) COMPARE-MS: METHOD RAPID, SENSITIVE AND ACCURATE DETECTION OF DNA METHYLATION

(75) Inventors: William G. Nelson, Towson, MD (US); Xiaohui S. Lin, Redland, CA (US); Angelo M. Demarzo, Baltimore, MD (US); Srinivasan Nasubramanian, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 12/159,081

(22) PCT Filed: Jan. 4, 2007

(86) PCT No.: PCT/US2007/000257
§ 371 (c)(1),
(2), (4) Date: Nov. 3, 2008

(87) PCT Pub. No.: WO2007/081791
PCT Pub. Date: Jul. 19, 2007

(65) Prior Publication Data
US 2009/0197263 A1    Aug. 6, 2009

Related U.S. Application Data

(60) Provisional application No. 60/755,980, filed on Jan. 4, 2006.

(51) Int. Cl.
*C12Q 1/68*     (2006.01)
*C07H 21/02*    (2006.01)
*C07H 21/04*    (2006.01)

(52) U.S. Cl. .......................... 435/6; 536/23.1; 536/24.3

(58) Field of Classification Search ............ 435/6, 91.2; 536/23.1, 24.3
See application file for complete search history.

(56) References Cited

U.S. PATENT DOCUMENTS

| | | | |
|---|---|---|---|
| 5,552,277 A * | 9/1996 | Nelson et al. ................ 435/6 |
| 5,972,614 A * | 10/1999 | Ruano et al. ................ 435/6 |
| 6,686,154 B2 * | 2/2004 | Nock et al. ................ 435/6 |
| 6,699,666 B1 | 3/2004 | Homma et al. | |
| 7,252,935 B2 * | 8/2007 | Sidransky ................ 435/6 |
| 7,358,048 B2 * | 4/2008 | Barany et al. ................ 435/6 |
| 7,405,044 B2 * | 7/2008 | Walker et al. ................ 435/6 |
| 7,425,415 B2 * | 9/2008 | Pfeifer et al. ................ 435/6 |
| 2003/0129602 A1 * | 7/2003 | Huang ................ 435/6 |
| 2003/0224040 A1 * | 12/2003 | Baylin et al. ................ 424/450 |
| 2004/0023279 A1 * | 2/2004 | Piepenbrock et al. ........... 435/6 |
| 2004/0086944 A1 * | 5/2004 | Grigg et al. ................ 435/7.1 |
| 2004/0146868 A1 * | 7/2004 | Cottrell et al. ................ 435/6 |
| 2005/0202490 A1 * | 9/2005 | Makarov et al. ................ 435/6 |
| 2005/0233364 A1 * | 10/2005 | Burgess et al. ................ 435/6 |
| 2005/0260630 A1 * | 11/2005 | Goodman et al. ............... 435/6 |
| 2005/0287553 A1 | 12/2005 | Guetig et al. | |
| 2006/0051768 A1 * | 3/2006 | Hoon et al. ................ 435/6 |
| 2006/0115460 A1 | 6/2006 | Naughton | |
| 2006/0246496 A1 * | 11/2006 | Ahmed et al. ................ 435/6 |
| 2007/0059753 A1 * | 3/2007 | Vener et al. ................ 435/6 |
| 2007/0117093 A1 * | 5/2007 | Tetzner et al. ................ 435/6 |
| 2008/0213791 A1 * | 9/2008 | Freije et al. ................ 435/6 |
| 2008/0249118 A1 * | 10/2008 | Hermeking et al. ........... 514/274 |
| 2009/0054260 A1 * | 2/2009 | Sidransky ................ 506/11 |
| 2009/0075251 A1 * | 3/2009 | Dietrich et al. ................ 435/6 |
| 2009/0099037 A1 * | 4/2009 | Baylin et al. ................ 506/10 |

OTHER PUBLICATIONS

Brock et al., A novel technique for the identification of CpG islands exhibiting altered methylation patterns (ICEAMP). Nucleic Acids Research 29 (24) : e123.*
Cross et al., Purification of CpG islands using a methylated DNA binding column. Nature Genet. 6 : 236-244 (1994).*
Rauch et al., Methylated-CpG island recovery assay: a new technique for the rapid detection of methylated-CpG islands in cancer. Laboratory Investigation 85 : 1172-1180 (Jul. 2005).*
Weber et al., Chromosome-wide and promoter-specific analyses identify sites of differential DNA methylation in normal and transformed human cells. Nature Genetics 37 (8) : 853-862 (Aug. 2005).*
Nan et al , Dissection of the methyl-CpG binding domain from the chromosomal protein MeCP2. Nucleic Acids Research 21(21) : 4886-4892 (1993).*
Enokida et al., CpG Hypermethylation of MDR1 Gene Contributes to the Pathogenesis and Progression of Human Prostate Cancer. Cancer Research 64 : 5956-5962 (2004).*
Gonzalgo et al., Prostate Cancer Detection by GSTP1 Methylation Analysis of Postbiopsy Urine Specimens. Clinical Cancer Research 9 : 2673-2677 (2003).*
Li et al., Age-dependent methylation of ESR1 gene in prostate cancer. BBRC 321 : 455-461 (2004).*
Yegnasubramanian et al., Hypermethylation of CpG Islands in Primary and Metastatic Human Prostate Cancer . Cancer Research 64 : 1975-1986 (2004).*
International Search Report WO 2007/081791 A3, Jul. 19, 2007, Nelson.

* cited by examiner

*Primary Examiner* — Ethan Whisenant
(74) *Attorney, Agent, or Firm* — DLA Piper LLP (US)

(57) ABSTRACT

The present invention provides methods and kits useful for enriching, identifying and quantifying methylated DNA3 particularly hypermethylated CpG islands by digesting a sample with a methylation-sensitive restriction endonuclease and capturing methylated restriction fragments with a methyl-binding capture reagent. The methods of the invention may be used in the detection of cancer, particularly detection of prostate cancer.

43 Claims, 6 Drawing Sheets

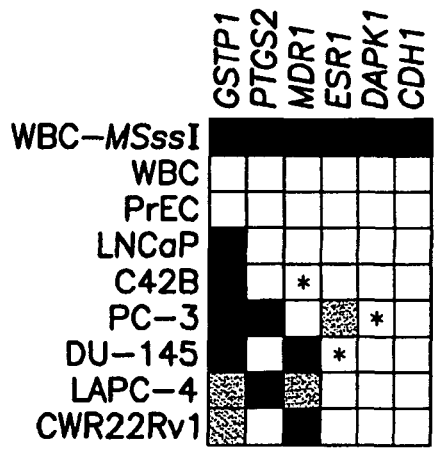
FIG. 4A
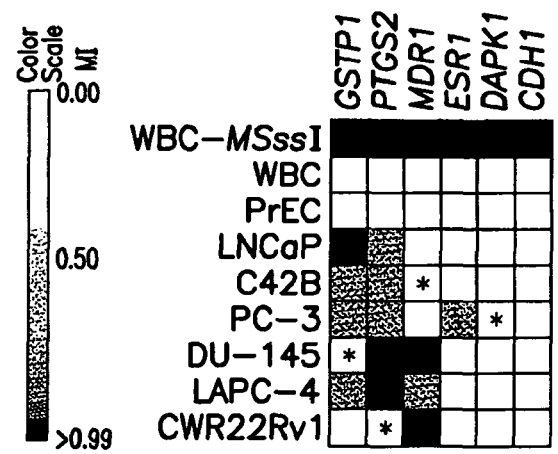
FIG. 4B
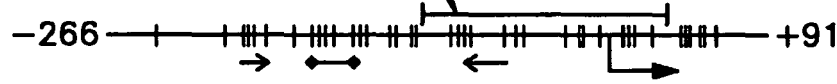
FIG. 4C
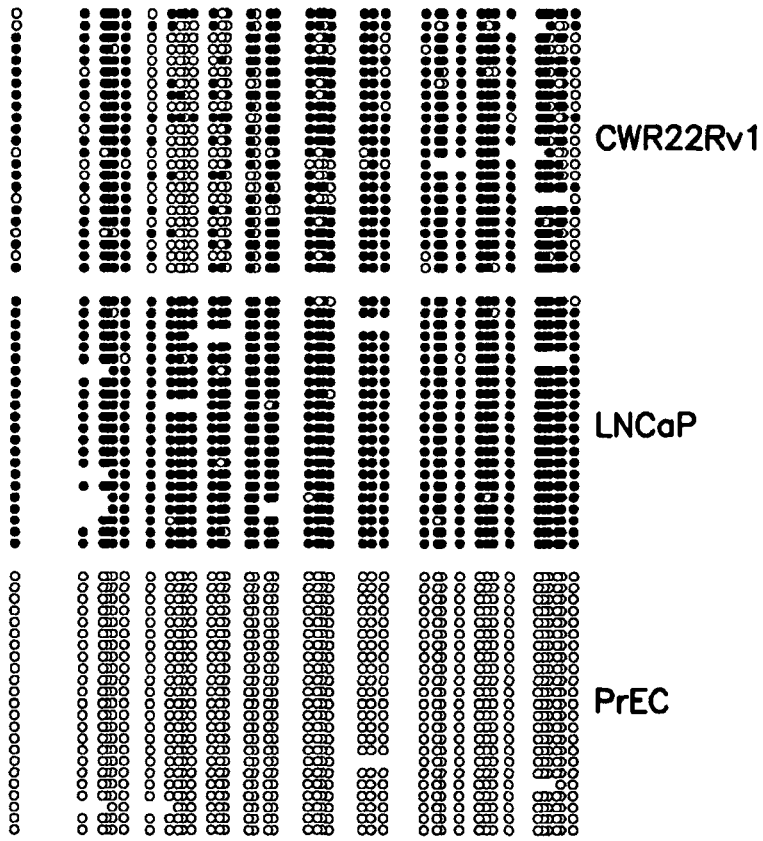
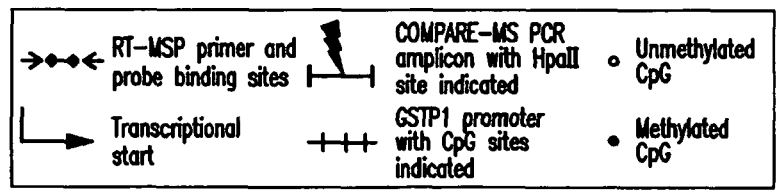

FIG. 5A  FIG. 5B
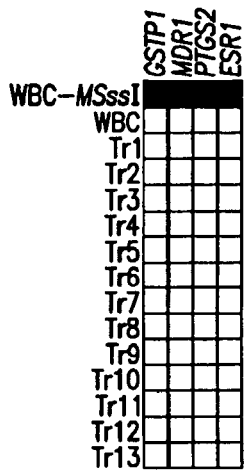
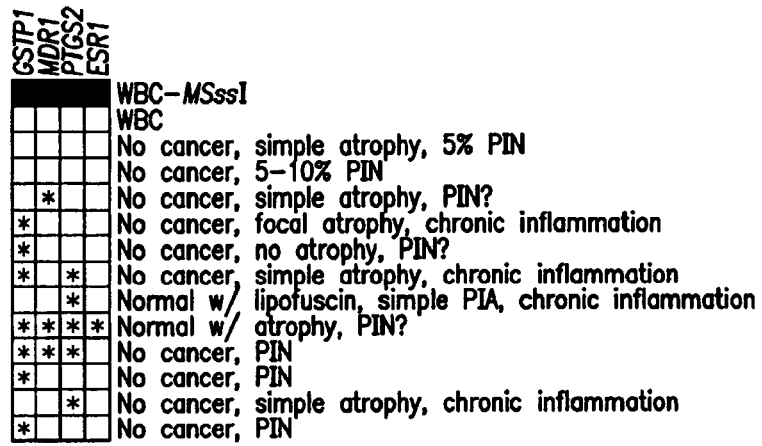
FIG. 5C
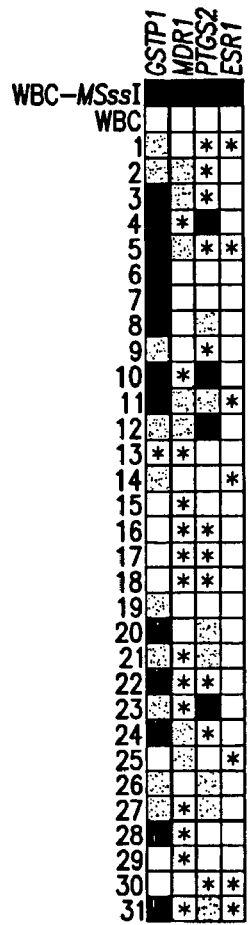
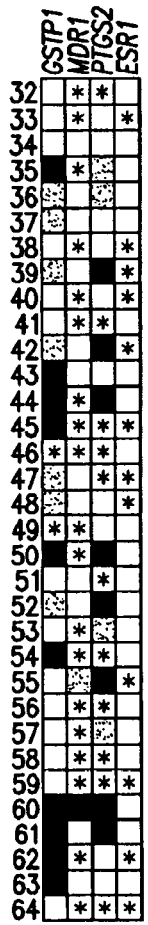
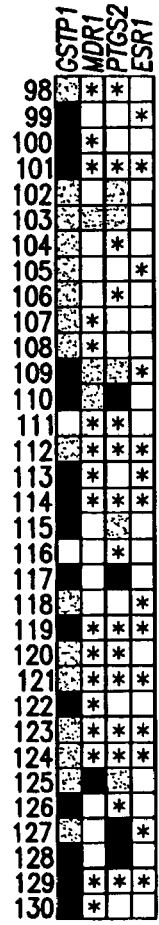
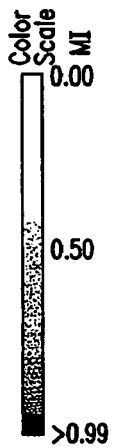

SEQUENCE LISTING

```
<160> NUMBER OF SEQ ID NOS: 20

<210> SEQ ID NO 1
<211> LENGTH: 29
<212> TYPE: DNA
<213> ORGANISM: Artificial sequence
<220> FEATURE:
<223> OTHER INFORMATION: Primer

<400> SEQUENCE: 1
ggatccatgg agagcgggaa gaggatgga                                          29

<210> SEQ ID NO 2
<211> LENGTH: 26
<212> TYPE: DNA
<213> ORGANISM: Artificial sequence
<220> FEATURE:
<223> OTHER INFORMATION: Primer

<400> SEQUENCE: 2
gaattccatc tttccagttc tgaagt                                             26

<210> SEQ ID NO 3
<211> LENGTH: 30
<212> TYPE: DNA
<213> ORGANISM: Artificial sequence
<220> FEATURE:
<223> OTHER INFORMATION: Synthetic construct

<400> SEQUENCE: 3
cgcggcagcc atcaccatca ccatcactaa                                         30
```

```
<210> SEQ ID NO 4
<211> LENGTH: 26
<212> TYPE: DNA
<213> ORGANISM: Artificial sequence
<220> FEATURE:
<223> OTHER INFORMATION: Synthetic construct

<400> SEQUENCE: 4
atcgtcgtac gttttcgtac gacgat                                         26

<210> SEQ ID NO 5
<211> LENGTH: 18
<212> TYPE: DNA
<213> ORGANISM: Artificial sequence
<220> FEATURE:
<223> OTHER INFORMATION: Primer

<400> SEQUENCE: 5
gggaccctcc agaagagc                                                  18

<210> SEQ ID NO 6
<211> LENGTH: 20
<212> TYPE: DNA
<213> ORGANISM: Artificial sequence
<220> FEATURE:
<223> OTHER INFORMATION: Primer

<400> SEQUENCE: 6
actcactggt ggcgaagact                                                20

<210> SEQ ID NO 7
<211> LENGTH: 20
<212> TYPE: DNA
<213> ORGANISM: Artificial sequence
<220> FEATURE:
<223> OTHER INFORMATION: Primer

<400> SEQUENCE: 7
ggagaggaag ccaagtgtcc                                                20

<210> SEQ ID NO 8
<211> LENGTH: 20
<212> TYPE: DNA
<213> ORGANISM: Artificial sequence
<220> FEATURE:
<223> OTHER INFORMATION: Primer

<400> SEQUENCE: 8
ggtttccgcc agatgtcttt                                                20

<210> SEQ ID NO 9
<211> LENGTH: 18
<212> TYPE: DNA
<213> ORGANISM: Artificial sequence
<220> FEATURE:
<223> OTHER INFORMATION: Primer

<400> SEQUENCE: 9
gtgggtggga ggaagcat                                                  18

<210> SEQ ID NO 10
<211> LENGTH: 20
<212> TYPE: DNA
<213> ORGANISM: Artificial sequence
<220> FEATURE:
<223> OTHER INFORMATION: Primer
```

```
<400> SEQUENCE: 10
tctccagcat ctccacgaag                                              20

<210> SEQ ID NO 11
<211> LENGTH: 20
<212> TYPE: DNA
<213> ORGANISM: Artificial sequence
<220> FEATURE:
<223> OTHER INFORMATION: Primer

<400> SEQUENCE: 11
ctcgggctgt gctcttttc                                               20

<210> SEQ ID NO 12
<211> LENGTH: 20
<212> TYPE: DNA
<213> ORGANISM: Artificial sequence
<220> FEATURE:
<223> OTHER INFORMATION: Primer

<400> SEQUENCE: 12
ccagatgctt tggtgtggag                                              20

<210> SEQ ID NO 13
<211> LENGTH: 18
<212> TYPE: DNA
<213> ORGANISM: Artificial sequence
<220> FEATURE:
<223> OTHER INFORMATION: Primer

<400> SEQUENCE: 13
cttgcagggt ccccattg                                                18

<210> SEQ ID NO 14
<211> LENGTH: 18
<212> TYPE: DNA
<213> ORGANISM: Artificial sequence
<220> FEATURE:
<223> OTHER INFORMATION: Primer

<400> SEQUENCE: 14
gtccggctgt cctcctca                                                18

<210> SEQ ID NO 15
<211> LENGTH: 20
<212> TYPE: DNA
<213> ORGANISM: Artificial sequence
<220> FEATURE:
<223> OTHER INFORMATION: Primer

<400> SEQUENCE: 15
caggtgaacc ctcagccaat                                              20

<210> SEQ ID NO 16
<211> LENGTH: 20
<212> TYPE: DNA
<213> ORGANISM: Artificial sequence
<220> FEATURE:
<223> OTHER INFORMATION: Primer

<400> SEQUENCE: 16
cacaggtgct ttgcagttcc                                              20

<210> SEQ ID NO 17
<211> LENGTH: 20
<212> TYPE: DNA
```

```
<213> ORGANISM: Artificial sequence
<220> FEATURE:
<223> OTHER INFORMATION: Primer

<400> SEQUENCE: 17
cgcagaagac gggtgatttc                                                    20

<210> SEQ ID NO 18
<211> LENGTH: 20
<212> TYPE: DNA
<213> ORGANISM: Artificial sequence
<220> FEATURE:
<223> OTHER INFORMATION: Primer

<400> SEQUENCE: 18
ccgtcacccc tttctttgac                                                    20

<210> SEQ ID NO 19
<211> LENGTH: 30
<212> TYPE: DNA
<213> ORGANISM: Artificial sequence
<220> FEATURE:
<223> OTHER INFORMATION: Primer

<400> SEQUENCE: 19
gttggtttta tgttgggagt tttgagtttt                                         30

<210> SEQ ID NO 20
<211> LENGTH: 31
<212> TYPE: DNA
<213> ORGANISM: Artificial sequence
<220> FEATURE:
<223> OTHER INFORMATION: Primer

<400> SEQUENCE: 20
atcctcttcc tactatctat ttactcccta a                                       31
```

COMPARE-MS: METHOD RAPID, SENSITIVE AND ACCURATE DETECTION OF DNA METHYLATION

CROSS REFERENCE TO RELATED APPLICATIONS

This application is a 35 USC §371 National Stage application of International Application No. PCT/US2007/000257 filed Jan. 4, 2007; which claims the benefit under 35 USC §119(e) to U.S. Application Ser. No. 60/755,980 filed Jan. 4, 2006, now abandoned. The disclosure of each of the prior applications is considered part of and is incorporated by reference in the disclosure of this application.

GRANT INFORMATION

This invention was made with government support under Grant Nos. CA070196 and CA113374 awarded by the National Institutes of Health. The United States government has certain rights in this invention.

FIELD OF THE INVENTION

This invention relates generally to the field of detecting DNA methylation, and particularly, hypermethylation of CpG islands. More specifically, the invention provides a method that combines methylation-sensitive restriction enzyme digestion with methyl-binding protein affinity capture to enrich, identify and quantify methylated sequences in DNA.

BACKGROUND OF THE INVENTION

DNA methylation, or the covalent addition of a methyl group to cytosine within the context of the CpG dinucleotide, has profound effects on the mammalian genome. These effects include transcriptional repression via inhibition of transcription factor binding or the recruitment of methyl-binding proteins and their associated chromatin remodeling factors, X chromosome inactivation, imprinting and the suppression of parasitic DNA sequences. DNA methylation is also essential for proper embryonic development; however, its presence can add an additional burden to the genome. Normal methylation patterns are frequently disrupted in tumor cells with global hypomethylation accompanying region-specific hypermethylation. When these hypermethylation events occur within the promoter of a tumor suppressor gene they may silence the gene and provide the cell with a growth advantage in a manner akin to deletions or mutations. Furthermore, DNA methylation may be an important player in both DNA repair and genome stability.

DNA methylation at the 5-position of cytosine in CpG dinucleotides is an important aspect of physiological processes including embryonic development, X chromosome inactivation, imprinting, and transcriptional regulation. While CpG dinucleotides are generally methylated throughout the genome of normal somatic cells, CpG islands (CGIs), clusters of CpG dinucleotides in gene regulatory regions, are usually unmethylated. Aberrant hypermethylation of CGIs and subsequent transcriptional repression is one of the earliest and most common somatic genome alterations in multiple human cancers. Some cancers even seem to exhibit a so-called CpG island methylator phenotype (CIMP). The rapid and sensitive detection of DNA hypermethylation, therefore, would not only enhance our understanding of how DNA methylation may contribute to carcinogenesis, but could aid in early cancer diagnosis and risk stratification.

Most of the current DNA methylation detection strategies use sodium bisulfite to deaminate cytosine to uracil while leaving 5-methylcytosine intact (Wang et al., *Nucleic Acids Res.*, 8:4777-90 (1980)). Among these, methylation specific PCR (MSP) (Herman et al., *Proc. Natl. Acad. Sci. USA*, 93:9821-26 (1996)) uses PCR primers targeting the bisulfite induced sequence changes to specifically amplify either methylated or unmethylated alleles. Quantitative variations of this technique, such as "MethyLight" (Eads et al., *Nucleic Acids Res.*, 28:E32 (2000)), "HeavyMethyl" (Cottrell et al., *Nucleic Acids Res.*, 32:e10 (2004)), and "MethylQuant" (Thomassin et al., *Nucleic Acids Res.*, 32:e168 (2004)), employ methylation specific oligonucleotides in conjunction with Taqman probes or SYBR Green based real-time PCR amplification to quantify alleles with a specific pattern of methylation. These techniques are highly sensitive and specific for detection of DNA methylation. However, bisulfite based techniques are quite cumbersome, involving time- and labor-intensive chemical treatments that damage DNA and limit throughput. Additionally, PCR primer design becomes difficult due to the reduction in genome complexity after bisulfite treatment, leading to an inability to interrogate the methylation pattern at some or all CpG dinucleotides in a genomic locus of interest.

Other DNA methylation detection assays use methylation-sensitive restriction enzymes to digest unmethylated DNA while leaving methylated DNA intact for detection by Southern blot analysis (Singer et al., *Science*, 203: 1019-1021 (1979); Bird & Southern, *J. Mol. Biol.*, 118:2747 (1978); Pollack et al., *Proc. Natl. Acad. Sci. USA*, 77:6463-67 (1980); Feinberg & Vogelstein, *Nature*, 301:89-92 (1983)), PCR (Singer-Sam et al., *Mol Cell Biol.*, 10:4987-89 (1990); Singer-Sam et al., *Nucleic Acids Res.*, 18:687 (1990)), or real-time PCR (Bastian et al, *Clin. Cancer Res.*, 11:4037-43 (2005)). The Southern blot strategy is not easily amenable to high throughput analysis, and requires copious amounts of high molecular weight DNA. Digestion followed by PCR is sensitive, but is limited to interrogating methylation only at the enzyme recognition sites and is plagued by a propensity for false-positives resulting from incomplete digestion.

Another strategy for in vitro methylation detection, first introduced in 1994 by Cross et al. (*Nat Genet*, 6: 23644), uses column- or bead-immobilized recombinant methylated-CpG binding domain (MBD) polypeptides, particularly MECP2 (Cross et al, supra; Brock et al., *Nucleic Acids Res.*, 29:E123 (2001); Shiraishi et al., *Proc. Natl. Acad. Sci. USA*, 96:2913-18 (1999)) and MBD2 (Rauch & Pfeifer, *Lab. Invest.*, 85:1172-80 (2005)), to enrich for methylated DNA fragments for subsequent detection by Southern Blot, PCR, or microarray hybridization. The MBD proteins are thought to bind specifically to methylated chromosomal DNA in mammalian cells (Ballestar et al., *EMBO J.*, 22:6335-45 (2003)), facilitating transcriptional silencing (Bakker et al., *J. Biol. Chem.*, 277:22573-80 (2002); Lin et al., *Cancer Res.*, 63:498-504 (2003)) by recruitment of chromatin remodeling and transcriptional repression complexes (Wade, *Bioessays*, 23:1131-37 (2001); Feng & Zhang, *Genes Dev.*, 15:827-32 (2001)). A recent version of this strategy, called MIRA (Rauch & Pfeifer, supra), uses fill-length MBD2 immobilized on magnetic beads to enrich for methylated DNA with subsequent detection of candidate methylated genes by PCR. Another assay, termed MeDIP (Weber et al., *Nat. Genet.*, 37:853-62 (2005)), uses bead-immobilized anti-5-methylcytosine antibodies (α5mC-Ab), instead of MBD proteins, to enrich for methylated DNA. However, the use of each these techniques has been limited by one or more of the following: a requirement for relatively large amounts of input genomic DNA, a potential for false-positive results due to capture of unmethylated DNA, incompatibility with high-throughput platforms, and lack of quantitative data.

Thus, there remains a need for methods that detect DNA methylation that are sensitive, accurate, and robust. The ability to multiplex samples, quantify levels of methylation at both the genomic and gene level, as well as the ability to perform analysis in high-throughput formats would be a clear advantage for methylation detection and identification methods used both in the research lab and in the clinic.

SUMMARY OF THE INVENTION

The present invention provides a method for enriching for methylated DNA by digesting a sample containing methylated DNA with a methylation-sensitive restriction endonuclease, such as HpaII. The method is particularly suited for enriching methylated DNA that contains methylated CpG islands. The sample can further be digested with a second restriction endonuclease such as AluI to reduce the size of the DNA fragments or reduce repetitive DNA. The methylated DNA fragments that are generated are then captured. Typically, the capture step involves contacting the methylated DNA restriction fragments with a reagent that binds methylated DNA, such as a methylated-CpG binding domain (MBD) polypeptide (e.g., MBD2 or a portion of MBD2 containing the methyl-binding domain) or an anti-5-methylcytosine antibody and separating bound DNA from unbound DNA. Typically, the capture reagent will be attached to a solid support such as a bead, especially a magnetic bead, a resin, a microtiter plate, a chip, or a test tube. In one aspect of the invention, the reagent is attached to the solid support through an affinity tag, such as a his tag. By capturing at least one of the methylated DNA fragments, the procedure enriches for methylated DNA, which can then be eluted from the solid support for further analysis.

The present method also provides a method for identifying a methylated DNA sequence in a sample. According to this method, a sample comprising the methylated DNA sequence is digested with a methylation-sensitive restriction endonuclease and the methylated DNA sequence is captured as above. The captured methylated DNA is then contacted with a reagent that identifies the sequence of the fragment, such as an oligonucleotide that selectively hybridizes to the methylated DNA sequence. The oligonucleotide can be a probe, extension primer or an amplification primer pair. In one embodiment, the methylated DNA sequence is amplified using the amplification primer pair, using, for example, polymerase chain reaction.

Also provided by the invention is a method for quantifying a methylated DNA sequence following the steps of digestion and capture as above. According to this method of the invention, the captured methylated DNA fragment is then contacted with a reagent that quantifies the methylated DNA sequence, such as an oligonucleotide that selectively hybridizes to the nucleotide sequence. Typically, the reagent will be an amplification primer pair that is used to quantitatively amplify the methylated DNA fragment. In certain embodiments, quantitative amplification is a real time quantitative polymerase chain reaction (QPCR).

The methods of the invention display a high degree of sensitivity. For example, methylated DNA sequences can be accurately quantified in samples containing as little as at least about 20-100 ng of DNA, such as at least about 30, 40, 50, 60, 70, 80 or 90 ng of DNA, with at least about 500, at least about 1000, at least about 2000, or at least about 3000 fold excess unmethylated DNA. The is the equivalent about 30 pg of the methylated DNA, which is the amount of s single copy gene present in about 5-6 cells.

The methods of the invention are also suitable for multiplexing, for example by detecting at least about 2, 3, 4, 5, 10, 50, 100, 500, 1000 or more sequences from the same sample, e.g. in parallel. Similarly, multiple sample can be processed at the same time, such as at least about 2, 3, 4, 5, 10, 50, 100, 500, 1000 different samples. The ease and speed with which the methods of the invention can be performed make them especially suited for high-throughput processing, such as processing by mechanical or robot devices.

In one embodiment of the invention, the methylation-sensitive restriction endonuclease digestion/methylated DNA capture methods can be used for detecting cancer in a subject, such as prostate cancer. According to this method, methylation of at least one DNA sequence is detected where hypermethylation of the DNA sequence is indicative of cancer. Detection of the sequence typically involves selectively hybridizing a primer pair, such as one of the pairs of SEQ ID NOS: 5 and 6, SEQ ID NOS: 7 and 8, SEQ ID NOS: 9 and 10, and SEQ ID NOS: 11 and 12, and amplifying the DNA which detect hypermethylation of CpG islands in GSTP1, MDR1, ESR1 and PTGS2 sequences.

In one aspect of this method, the methylated (hypermethylated) DNA sequence is quantified in the sample and a methylation index for the sequence is calculated. The methylation index is a measure of the amount or degree of methylation of a particular sequence and is calculated as the ratio of ratio of the amount of methylated alleles of the sequence to the amount of methylated alleles of the same sequence in a maximally methylated control sample (e.g., one that has been treated with M.SssI.). For prostate cancer, a methylation index >0.2 will typically indicate cancer, although a methylation index at least three standard deviations greater than the background can also be indicative of cancer, particularly when the sample is a tumor adjacent tissue.

Also provided are kits useful for performing methods of the invention. The kit typically include a first container containing a methylation-sensitive restriction endonuclease; and a second container containing a MBD capture reagent. Kits for identifying hypermethylated DNA sequences may also contain at least one pair of primers for amplification of the hypermethylated DNA sequence. For quantification purposes, the kits can also include a control DNA sample the hypermethylated DNA sequence treated with M.SssI.

Kits useful for detecting cancer, particularly prostate cancer include primer pairs that detect DNA sequences that are hypermethylated in prostate cancer, such as pairs of primers having the sequences set forth in SEQ ID NOS: 5 and 6, SEQ ID NOS: 7 and 8, SEQ ID NOS: 9 and 10, and SEQ ID NOS: 11 and 12, which detect GSTP1, MDR1, ESR1 and PTGS2.

BRIEF DESCRIPTION OF THE FIGURES

FIG. 3 illustrates COMPARE-MS assay performance.

FIG. 4 illustrates the validation of COMPARE-MS by analysis of hypermethylation at 6 gene-specific CGIs in multiple prostate cell lines. FIG. 4A Methylation index (MI), defined as the ratio of the amount of methylated alleles in a given sample to the amount of methylated alleles in the same input quantity of M.SssI treated WBC DNA, as determined by COMPARE-MS, for six cancer-related genes (GSTP1, PTGS2, MDR1, ESR1, DAPK1, CDH1) in 20 ng of genomic DNA from 6 prostate cancer cell lines (LNCaP, C42B, PC-3, DU-145, LAPC-4, and CWR22Rv1), one primary culture model of non-malignant prostate epithelial cells (PrEC), and untreated WBC negative control. FIG. 4B. MI for the same set of CGIs and samples as determined by an alternative assay (MethyLight) for comparison. With few exceptions, the CGI hypermethylation pattern obtained from COMPARE-MS, shown in FIG. 4A, is highly similar to those obtained from MethyLight as shown in FIG. 4B. *, denotes MI<0.2 but at least 3 standard deviations greater than the background level seen in 10 identical replicates of WBC samples. These data demonstrate the applicability of COMPARE-MS to heterogeneous human tissue samples. FIG. 4C shows the results of bisulfite genomic sequencing of the GSTP1 CGI in PrEC, LNCaP and CWR22Rv1 cell lines. The bisulfite sequencing results show that COMPARE-MS was accurate in identifying that the GSTP1 CGI in CWR22Rv1 cells is highly methylated, and demonstrates that MethyLight failed to detect this because many of the CpG dinucleotides interrogated by the methylation specific primers and probe were mostly unrethylated. Both COMPARE-MS and MethyLight were able to correctly identify that LNCaP and PrEC cells were homogeneously methylated and unmethylated respectively. The indicated bisulfite sequencing start and end positions are relative to the transcriptional start site.

FIG. 5 illustrates COMPARE-MS applied to heterogeneous prostate tissues. MI at the GSTP1, MDR1, PTGS2, and ESR1 CGIs in the following samples. FIG. 5A: 20 ng of genomic DNA from benign prostate tissues obtained from 13 organ donors, who had no evidence of prostatic malignancies. FIG. 5B: 20 ng of genomic DNA from tumor-adjacent benign prostate cancer tissues isolated from 12 of the 130 men from whom prostates were obtained during radical prostatectomy for treatment of primary prostate cancer. FIG. 5C: 20 ng of genomic DNA from primary prostate cancer tissues from 130 primary prostate cancer patients undergoing radical prostatectomy for treatment of their disease. *, denotes MI<0.2 but greater than the threshold determined by ROC curve analysis. These data demonstrate the applicability of COMPARE-MS to heterogeneous human tissue samples.

DETAILED DESCRIPTION OF THE INVENTION

Figure 1:
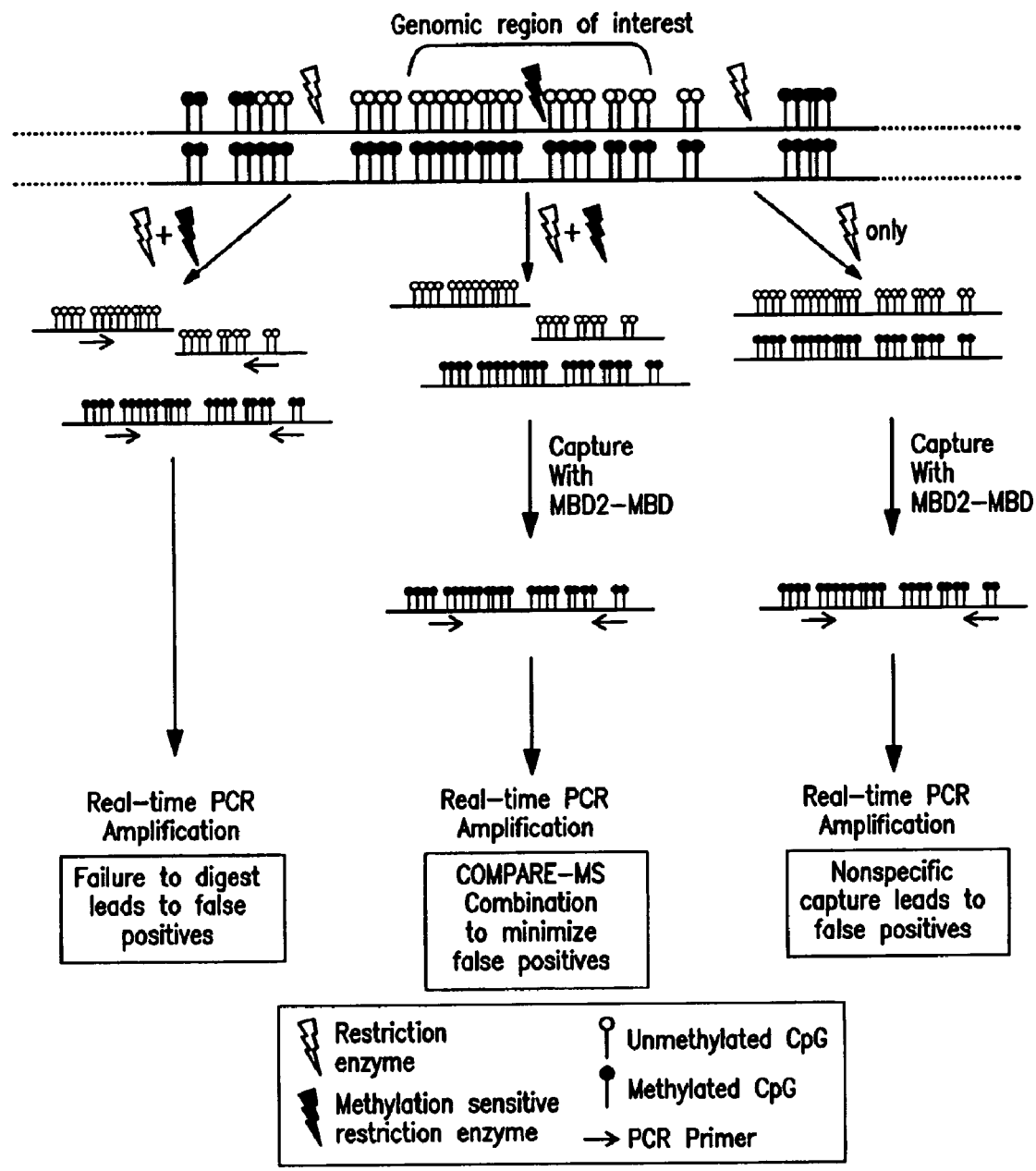
FIG. 1 shows an overview and the rationale for the COMPARE-MS assay. Genomic DNA is digested with AluI with or without the methylation-sensitive restriction enzyme HpaII. After digestion, either the MBD2-MBD captured methylated DNA or all digested DNA are subjected to real-time PCR at a gene-specific locus. Although enrichment of methylated DNA by methylation-sensitive restriction enzyme digestion alone or by MBD2-MBD capture of methylated DNA alone may result in false positives associated with incomplete digestion or nonspecific capture respectively, the combination of the two approaches (COMPARE-MS) maintains sensitivity while minimizing false positive results.

Before the present compositions and methods are described, it is understood that this invention is not limited to the particular methodology, protocols, and reagents described as these may vary. It is also to be understood that the terminology used herein is for the purpose of describing particular embodiments only, and is not intended to limit the scope of the present invention which will be described by the appended claims.

It must be noted that as used herein and in the appended claims, the singular forms "a", "an", and "the" include plural reference unless the context clearly dictates otherwise. Thus, for example, reference to "a subject" includes a plurality of such subjects, reference to "a DNA sequence" includes one or more DNA sequences and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the methods, devices, and materials are now described. All publications mentioned herein are incorporated herein by reference for the purpose of describing and disclosing the proteins, compounds, and methodologies which are reported in the publications which might be used in connection with the invention. Nothing herein is to be construed as an admission that the invention is not entitled to antedate such disclosure by virtue of prior invention.

This present invention provides a DNA methylation assay that greatly enriches for methylated DNA by combining two independent and complementary strategies: 1) digestion with a methylation-sensitive restriction enzymes; and 2) specific capture of methylated DNA by binding to an affinity reagent, such as MBD polypeptides immobilized on a magnetic solid matrix.

In one embodiment, the present invention provides methods for enriching samples for methylated DNA, particularly hypermethylated DNA such as CpG island-containing sequences. The enriched methylated DNA can then be subjected to sequence-specific amplification to identify individual methylated DNA sequences, such as genes or gene regulatory regions. In certain embodiments, sequence-specific amplification of captured DNA can provide quantitative measurements of methylation status for particular methylated sequences.

In certain aspects, the assay of the invention is referred to as "Combination of Methylated-DNA Precipitation and Methylation Sensitive Restriction Enzymes" or "COMPARE-MS."

The methods of the invention are based on the observation that a combination of two strategies (digestion with methylation-sensitive restriction and methyl-binding domain assisted capture to enrich methylated DNA) complement each other by eliminating many of the problems associated with using either technique alone, while achieving sensitivities and specificities comparable to bisulfite treatment based PCR techniques (e.g., MSP, MethyLight, and others). Furthermore, the combination avoids the disadvantages of bisulfite treatment. Additionally, the methods of the present invention are highly amenable to high-throughput, (e.g., 96-well plate analysis; mechanical or robotic processing), and multiplexing for rapid determination of quantitative methylation and hypermethylation patterns at multiple CGIs simultaneously.

As used herein, a "methylation sensitive restriction endonuclease" is a restriction endonuclease that includes CG as part of its recognition site and has altered activity when the C is methylated as compared to when the C is not methylated. Methylation-sensitive restriction enzymes suitable for use in the present invention typically cleave restriction sites that contain unmethylated CpG, but do not cleave sites containing methylated CpG. Any restriction endonuclease that includes CG as part of its recognition site and that is inhibited when the C is methylated, can be utilized. Restriction enzymes that are sensitive to CpG methylation include, but are not limited to, Aat II, Aci I, Acl I, Afe I, Age I, Asc I, AsiS I, Ava I, BceA I, BmgB I, BsaA I, BsaH I, BsiE I, BsiW I, BsmB I, BspD I, BspE I, BsrB I, BsrF I. BssH II, BstB I, BstU I, Cla I, Eag I, Fau I, Fse I, Fsp I, Hae II, Hga I, Hha I, HinP1 I, Hpa II, Hpy99 I, HpyCH4 IV, Kas I, Mlu I, Nae I, Nar I, NgoM IV, Not I, Nru I, PaeR7 I, Pml I, Pvu I, Rsr II, Sac II, Sal I, Sfo I, SgrA I, Sma I, SnaB I, Til I, and Xho I.

In certain embodiments, the methylation sensitive restriction endonucleases that can be used to enrich for 5'CpG methylation include SmaI, SacII, EagI, MspI, HpaII, BstUI and BssHII. In one embodiment of the invention, the methylation-sensitive restriction enzyme step uses HpaII, which recognizes a site that is abundant in most CGIs. However, the invention contemplates the use of any methylation-sensitive restriction enzyme, particularly those that recognize unmethylated sites found in CGIs. The skilled artisan will be well aware of how to select a suitable methylation-sensitive restriction enzyme. For example, where larger segments of DNA are required, an enzyme that recognizes a 6- or 8-base recognition sequence may be used. In other embodiments, a shorter fragment size may be desired and this can be accomplished by choosing a methylation sensitive restriction endonuclease with a 4-base recognition site.

In certain embodiments of the methods of the invention, the DNA can be digested with one or more additional restriction enzymes in order to generate shorter fragments of DNA or digest repetitive DNA fragments. Carrying out the methods of the invention with shorter fragments of DNA may facilitate enrichment of methylated DNA and ease of sample handling. One non-limiting example of a restriction enzyme suitable for use as a second enzyme in the methods of the present invention is AluI, which recognizes the sequence 5'-AGCT-3' found in certain repetitive genomic DNA sequences.

The second step of the method for enriching methylated DNA involves capturing at least one of the DNA fragment(s) generated by methylation-sensitive restriction endonuclease digestion. As used herein, "capture" or "capturing" refers to the selective partitioning or sequestering of methyl-containing DNA fragments. Typically, the capturing step involves selectively immobilizing methylated DNA via interaction with a methylated DNA binding species ("capture reagent") that is attached to a solid substrate. Uncaptured DNA (e.g., unmethylated or hypomethylated DNA) can then be separated from the captured species by a physical separation procedure, such as washing, centrifugation or precipitation.

The capture step is similar to previously reported methods based on affinity binding to a captured species. Methods for capturing methylated DNA include, but are not limited to, MIRA (Rauch & Pfeifer, supra), MeDIP (Weber et al., supra), and MECP2-MBD columns (Brock et al., supra; Shiraishi et al., *Proc. Natl. Acad. Sci. USA,* 96:2913-2918 (1999); Rauch & Pfeifer, supra).

In one embodiment of the invention, capture is performed by contacting methylated restriction fragments with a capture reagent that binds to methylated DNA, particularly methylated CpG islands. For example, methylated DNA can be contacted with a methyl-CpG-binding domain (MBD) polypeptide, such as MBD1, MBD2, MBD3, MBD4, or MBD5 (Hendrich & Bird, *Mol. Cell. Biol.* 18:6538-47 (1998)), MeCP2 (Nan et al., *Nucleic Acids Res.,* 21, 4886-92 (1993)), or Kaiso (Filion et al., *Mol. Cell. Biol.,* 26:169-181 (2006)). Recombinant MBD polypeptides are also suitable for use in the capture step, including MBD species having multimerized and/or improved methyl-binding capacities. For example, Jørgensen et al., reported multimerization of the MBD domain of MBD1 polypeptide, leading to a species that binds methyl-CpG with a dissociation constant that is >50-fold higher than that the monomer. (Jørgensen et al., *Nucleic Acids Res.,* 34:e96 (2006))

Particularly useful MBDs include chimeric polypeptides containing an affinity or epitope tag, such as a poly-His, GST, HA, Flag, myc, or other tag well known in the art. Such tags allow the protein to be conveniently isolated and purified through the interaction of the affinity or epitope tag with a cognate binding species, which can be a metal ion, glutathione, anti-HA antibody, anti-Flag antibody or anti-myc antibody, respectively, for the tags listed above. Furthermore, the affinity tag can be used to anchor the MBD polypeptide to a solid support, such as a nickel-resin in the case of a his-tagged protein. Also contemplated by the invention are tags or other modifications that may be added to the protein post-synthetically. For example, the MBD can be biotinylated for affinity purification and immobilization using avidin or streptavidin reagents.

In one embodiment, the present invention relies on the specific binding of an MBD polypeptide to methylated DNA in order to capture restriction fragments containing methylated sequences. One of ordinary skill in the art will appreciate that the MBD polypeptides used in the present invention can be manipulated in order to increase the stability of MBD-DNA complex and to have other useful or desirable properties. Such manipulations are contemplated herein, so long as the MBD polypeptide retains the ability to bind methylated DNA.

Thus, in one embodiment, the MBD polypeptide of the present invention is a recombinant, chimeric or fusion protein, expressed in vitro or in vivo. The nucleic acid encoding the MBD may be incorporated into an expression vector, which may be either a self-replicating extrachromosomal vector, a vector which integrate into a host genome, or a linear nucleic acid that may or may not self-replicate. Thus, specifically included within the definition of expression vectors are linear nucleic acid molecules. Expression vectors thus include plasmids, plasmid-liposome complexes, phage vectors, and viral vectors, e.g., adeno-associated virus (AAV)-based vectors, retroviral vectors, herpes simplex virus (HSV)-based vectors, and adenovirus-based vectors. The nucleic acid molecule and any of these expression vectors can be prepared using standard recombinant DNA techniques described in, for example, Sambrook et al., "Molecular Cloning, a Laboratory Manual" 2d edition, Cold Spring Harbor Press, Cold Spring Harbor, N.Y. (1989), and Ausubel et al., "Current Protocols in Molecular Biology," Greene Publishing Associates and John Wiley & Sons, New York, N.Y. (1994).

Generally, MBD expression vectors contain a sequence encoding all or part of a methyl-binding polypeptide, particularly the methyl-binding domain. In one embodiment, the MBD polynucleotide is a cDNA sequence of human MBD2 (MBD2-MBD) amplified by PCR from clone MGC-45084 (American Type Culture Collection), using PCR primers 5'-GGATCCATGGAGAGCGGGAAGAGGATGGA-3' (SEQ ID NO:1) and 5'-GAATTCCATCTTTCCAGTTCT-GAAGT-3' (SEQ ID NO:2), containing BamHI and EcoRI recognition sites.

Typically expression vectors of the invention include transcriptional and translational regulatory nucleic acid sequences operably linked to the nucleic acid encoding the MBD polypeptide. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

A nucleic acid is "operably linked" when it is placed into a functional relationship with another nucleic acid sequence. For example, DNA for a presequence or secretory leader is operably linked to DNA encoding a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the MBD polypeptide, as will be appreciated by those in the art; for example, transcriptional and translational regulatory nucleic acid sequences from Baculovirus are preferably used to express the MBD protein in insect cells. Numerous types of appropriate expression vectors, and suitable regulatory sequences are known in the art for a variety of host cells.

In general, the transcriptional and translational regulatory sequences can include, but are not limited to, promoter sequences, ribosomal binding sites, transcriptional start and stop sequences, translational start and stop sequences, and enhancer, silencer, or activator sequences. In a preferred embodiment, the regulatory sequences include a promoter and transcriptional start and stop sequences.

A "promoter" is a nucleic acid sequence that directs the binding of RNA polymerase and thereby promotes RNA synthesis. Promoter sequences include constitutive and inducible promoter sequences. Exemplary constitutive promoters include, but are not limited to, the CMV immediate-early promoter, the RSV long terminal repeat, mouse mammary tumor virus (MMTV) promoters, etc. Suitable inducible promoters include, but are not limited to, the IL-8 promoter, the metallothionine inducible promoter system, the bacterial lac-ZYA expression system, the tetracycline expression system, and the T7 polymerases system. The promoters can be either naturally occurring promoters, hybrid promoters, or synthetic promoters. Hybrid promoters, which combine elements of more than one promoter, are also known in the art, and are useful in the present invention.

In addition, the expression vector can comprise additional elements. For example, the expression vector may have two replication systems (e.g., origins of replication), thus allowing it to be maintained in two organisms, for example, in animal cells for expression and in a prokaryotic host for cloning and amplification. Furthermore, for integrating expression vectors, which are generally not preferred in most embodiments, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors and appropriate selection and screening protocols are well known in the art and are described in e.g., Mansour et al., (*Cell* 51:503 (1988)), and Murray, ("Gene Transfer and Expression Protocols," Methods in Molecular Biology, Vol. 7 (Clifton: Humana Press, 1991)).

In addition, in certain embodiments, the expression vector contains a selection gene to allow the selection of transformed host cells containing the expression vector, and particularly in the case of mammalian cells, ensures the stability of the vector, since cells which do not contain the vector will generally die. Selection genes are well known in the art and will vary with the host cell used. By "selection gene" herein is meant any gene which encodes a gene product that confers new phenotypes of the cells which contain the vector. These phenotypes include, for instance, enhanced or decreased cell growth. The phenotypes conferred by selection genes also can include resistance to a selection agent. Further, the cell phenotypes conferred by a selection agent also include altered biochemical activities upon disruption of cell membrane. Suitable selection agents include, but are not limited to, neomycin (or its analog G418), blasticidin S, histinidol D, bleomycin, puromycin, hygromycin B, and other drugs. The expression vector also can comprise a coding sequence for a marker protein, such as the green fluorescence protein, which enables, for example, rapid identification of successfully transduced cells.

In one embodiment, the expression vector contains a RNA splicing sequence upstream or downstream of the gene to be expressed in order to increase the level of gene expression.

Recombinant MBD polypeptides and fusion proteins of the present invention can be produced by culturing a host cell transformed with nucleic acid, preferably an expression vector as outlined herein, under the appropriate conditions to induce or cause production of the fusion protein. The conditions appropriate for fusion protein production will vary with the choice of the expression vector and the host cell, and will be easily ascertained by one skilled in the art using routine methods. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cells are lytic viruses, and thus harvest time selection can be crucial for product yield.

Any host cell capable of withstanding introduction of exogenous DNA and subsequent protein production may be suitable for the present invention. Appropriate host cells include yeast, bacteria, archaebacteria, plant, and insect and animal cells, including mammalian cells and particularly human cells. The host cells may be native cells, primary cells, including those isolated from diseased tissues or organisms, cell lines (such as, for example, those originating with diseased tissues), genetically altered cells, etc. Of particular interest are *Drosophila melanogaster* cells, *Saccharomyces cerevisiae* and other yeasts, *E. coli, Bacillus subtilis*, SF9 cells, C129 cells, 293 cells, *Neurospora*, BHK, CHO, COS, and HeLa cells, fibroblasts, Schwanoma cell lines, etc. See the ATCC cell line catalog, hereby expressly incorporated by reference. In one embodiment, the MBD polypeptides are expressed in insect cells, such as Sf9 cells. Expression vectors for the transformation of insect cells, and in particular, baculovirus-based expression vectors, are well known in the art and are described e.g., in O'Reilly et al., "Baculovirus Expression Vectors: A Laboratory Manual" (New York: Oxford University Press, 1994).

Methods of introducing exogenous nucleic acid into host cells are well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In addition to the components outlined herein, MBD expression vectors may comprise a number of additional components, including, control sequences, selection genes, activatible elements, recombination signals and labels.

In certain embodiments, the MBD expression vectors contain a sequence encoding an affinity tag, such as a polyhistidine encoding sequence. In one embodiment of the invention, a modified pFastBac 1 baculovirus expression vector (Invitrogen), pFBC6H generated by inserting the sequence 5'-CGCGGCAGCCATCACCATCACCATCAC-TAA-3'(SEQ ID NO:3), which encodes a 6-histidine tag, into pFastBac™ I between the EcoRI and XbaI sites is used to clone the MBD and generate a fusion polypeptide thereof containing a 6×-his tag.

In certain embodiments of the invention, the methyl-binding reagent can be an antibody, such as an anti-5-methylcytosine monoclonal or polyclonal antibody, or antigen binding fragment thereof. "Antibody" as used herein includes intact immunoglobulin molecules (e.g., IgG1, IgG2a, IgG2b, IgG3, IgM, IgD, IgE, IgA), as well as fragments thereof, such as Fab, F(ab')2, scFv, and Fv, which are capable of specific binding to a methylated DNA epitope such as 5-methylcytosine. "Antibody fragments" comprise a portion of a full length antibody, generally the antigen binding or variable region thereof. Examples of antibody fragments include Fab, Fab', F(ab')2, and Fv fragments; diabodies; linear antibodies; single-chain antibody molecules; and multispecific antibodies formed from antibody fragments. Fragments of antibodies suitable for use in capture methods and methods for producing such fragments are well known in the art, including Fv fragments (Skerra & Pluckthun, *Science* 240:1038 (1988)), single-chain Fv fragments ("scFv;" Bird et al., *Science* 242: 423 (1988); Huston et al., *Proc. Natl. Acad. Sci. USA*, 85:5879 (1988)) and Fab fragments (Better et al., *Science* 240:1041 (1988)).

Portions, domains or fragments of MBD polypeptides are also suitable for use in the capture step of the methods of the present invention. The use of smaller fragments that retain an MBD domain (i.e. that binds methylated DNA) may prove advantageous over other reagents for the capture and enrichment of methylated DNA. For example, using just the small ~10 kD MBD portion of the MBD2 protein, as opposed to the full length protein, may eliminate unwanted interactions between unmethylated DNA and other domains on the MBD2 protein. "Fragment," as used herein, refers to a portion or section of a polypeptide and can be produced by any method known in the art, including, but not limited to protease digestion, physical fragmentation, expression of PCR products expression of regions of a polypeptide. An MBD fragment, such as MBD2-MBD (described in Example 1, below), can be produced by any method available in the art, including for example, protease digestion of an intact MBD polypeptide. In one embodiment, the MBD fragment is expressed using recombinant DNA technology from a template polynucleotide containing a nucleic acid sequence encoding the MBD fragment. Conveniently, the template can be fused in frame to sequences encoding an epitope or affinity tag as described above, to facilitate purification as described above. In one embodiment of the invention, the capture reagent is MBD2-MBD containing a 6-his tag, as described below in Example 1.

MBD2-MBD has high affinity and specificity for symmetrically methylated DNA templates. Previous studies have also shown that of all the known MBD proteins, MBD2 has the highest affinity for a wide range of methylated DNA sequences, including double stranded methylated DNA (Fraga et al., *Nucleic Acids Res.*, 31:1765-74 (2003), while the prototype methyl-CpG-binding protein (MeCP2) binds selectively to a single symmetrically methylated CpG sequence, and may selectively bind to CpG dinucleotides adjacent to A/T rich sequences (Klose et al., *Mol. Cell*, 19:667-78 (2005)). In certain aspects of the invention, the capture reagent is an MBD domain-containing polypeptide that binds double stranded methylated DNA, such as MBD2-MBD. Such double-stranded binding polypeptides and fragments thereof may be more suited for certain enrichment applications than other reagents. For example, where tight binding of methylated DNA to the capture reagent is required, particularly where the methylated DNA has high G/C content (e.g. CGIs), which may be resistant to denaturing and prone to forming secondary structures even after denaturing, double strand DNA binding may provide optimal capture. In other embodiments, a capture reagent which only binds to single stranded DNA, such as certain anti-5-methylcytosine antibodies (Weber et al., supra) may be suitable.

The capture reagent is typically immobilized on a solid support, which can be accomplished by any conventional means, e.g., absorption, covalent binding with a crosslinking agent, or covalent linkage resulting from chemical activation of either or both of the support or the capture reagent. Immobilization of the capture reagent may be also be accomplished indirectly by immobilizing one half of a binding pair, e.g., streptavidin, to the support and binding the other half of the same binding pair, e.g., biotin, to the capture reagent.

In one embodiment of the invention, the capture reagent an MBD polypeptide that is expressed or synthesized to include is a poly-histidine tag that will interact with immobilized metal ions, such as nickel. In addition, the poly-his tag can be recognized by antibodies directed to the tag.

A solid support according the invention may be any material that can be physically separated from unbound DNA in solution, including but not limited to beads, resin, microspheres, microtiter plate wells, test tubes, glass slides, chips and the like. In one aspect of the invention, the capture reagent is immobilized on magnetic beads. Separation of the beads and any bound DNA species from unbound species can easily and rapidly be accomplished using a magnet or magnetized device.

Once captured, methylated DNA can analyzed in situ or can be eluted from the solid support. The skilled artisan will be aware of various methods for eluting the DNA from the solid support by dissociation of the MBD-DNA interaction, such as treatment with detergent, high salt concentrations, chaotropic ions and/or heat. In one embodiment, the DNA is eluted from the solid support by boiling. In another embodiment, heating to at least about 90° C. is used. In another embodiment, the temperature used for elution is at least about 95° C.

Eluted DNA can be analyzed by any method known in the art, including quantification by UV spectroscopy or a calorimetric assay, restriction digestion, hybridization, electrophoresis, sequence analysis, amplification, cloning, mass spectrometry, and the like. The skilled artisan will appreciate that the uncaptured "flow-through" DNA, which is unmethylated, hypomethylated, or methylated to a lesser extent than the captured DNA, can also be analyzed by any of the methods described herein. In certain embodiments, the captured and flow-through DNA are referred to as methylation-enriched ("methylated") and methylation-depleted ("unmethylated"), respectively.

The present invention also provides methods for identifying methylated sequences present in a sample. The sample of the present invention can be any sample suitable for the methods provided by the present invention. In one aspect, the sample contains nucleic acid, particularly DNA, that is or is suspected of containing methylated sequences. In another aspect, the sample contains hypermethylated DNA sequences and/or DNA containing methylated CpG islands. In one embodiment, the sample of the present invention is a biological sample, such as a tissue sample, e.g., a biopsy specimen such as samples from needle biopsy. In another embodiment, the biological sample of the present invention is a sample of bodily fluid, e.g., serum, plasma, urine, saliva, sputum or ejaculate. In yet another embodiment, the sample contains blood cells, such as white blood cells.

If the sample is impure (such as plasma, serum, or blood), it may be treated before use with an amount of a reagent effective to open the cells, fluids, tissues, or animal cell membranes of the sample, and to expose the nucleic acid. This lysing will allow digestion and capture to occur much more readily. In some embodiments, further purification of the DNA from the sample may be required. Methods for purifying DNA, such as genomic DNA, from cells, fluids and tissues will be well known to the skilled artisan.

Identification of a particular sequence in the captured methylated DNA can be accomplished by any method, including but not limited to hybridization, (e.g., Southern blotting), primer extension, and direct sequence determination. Typically, identification of a methylated DNA sequence will include the step of contacting captured methylated DNA fragments with a reagent that identifies the sequence of the fragment, such as an oligonucleotide probe or primer. In one aspect of the invention, the methylated DNA is contacted with the oligonucleotide probe or primer and selective hybridization of the primer or probe is detected. Selective hybridization of a probe can also be detected, by detectably labeling the probe, and detecting the presence of the label using a blot type analysis such as Southern blot analysis. Selective hybridization of a primer can be detected, for example, by performing a primer extension reaction, and detecting a primer extension reaction product comprising the primer. In one embodiment of the invention, the methylated DNA sequence is identified using at least one pair of primers that selectively hybridizes to the sequence. In certain aspects, the pair of primers is used to amplify the sequence and the amplification product is detected, e.g., by electrophoresis or autoradiography as an indication of selective hybridization.

As used herein, the term "selective hybridization" or "selectively hybridize" or "specific hybridization" refers to an interaction of two nucleic acid molecules that occurs and is stable under moderately stringent or highly stringent conditions. As such, selective hybridization preferentially occurs, for example, between an oligonucleotide and a target nucleic acid molecule, and not substantially between the oligonucleotide and a nucleic acid molecule other than the target nucleic acid molecule.

The primers of the invention embrace oligonucleotides of sufficient length and appropriate sequence so as to provide specific initiation of polymerization on a significant number of nucleic acids in the polymorphic locus. Specifically, the term "primer" as used herein refers to a sequence comprising two or more deoxyribonucleotides or ribonucleotides, preferably more than three, and most preferably more than 8, which sequence is capable of initiating synthesis of a primer extension product. Environmental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent for polymerization. The exact length of primer will depend on many factors, including temperature, buffer, and nucleotide composition.

Generally, an oligonucleotide useful as a probe or primer that selectively hybridizes to a target nucleic acid molecule is at least about 12 to 15 nucleotides in length, generally at least about 18 to 20 nucleotides in length, usually at least about 21 to 25 nucleotides in length, and particularly about 26 to 35 nucleotides in length or. Examples of oligonucleotides useful in practicing the methods of the invention are disclosed herein in Table 1 (SEQ ID NOS:5 to 18).

Conditions that allow for selective hybridization can be determined empirically, or can be estimated based, for example, on the relative GC:AT (or GC:AU) content of the hybridizing oligonucleotide and the target nucleic acid molecule, the length of the hybridizing oligonucleotide, and the number, if any, of mismatches between the oligonucleotide and target sequence to which it is to hybridize (see, for example, Sambrook et al., "Molecular Cloning: A Laboratory Manual" (Cold Spring Harbor Laboratory Press 1989)). As such, the conditions used to achieve a particular level of stringency will vary, depending on the nature of the hybridizing nucleic acid molecules. An additional consideration is whether one of the nucleic acids is immobilized, for example, on a filter. An example of progressively higher stringency conditions is as follows: 2×SSC/0.1% SDS at about room temperature (hybridization conditions); 0.2×SSC/0.1% SDS at about room temperature (low stringency conditions); 0.2× SSC/0.1% SDS at about 42° C. (moderate stringency conditions); and 0.1×SSC at about 62° C. (high stringency conditions). Hybridization and/or washing can be carried out using only one of these conditions, for example, high stringency conditions, or each of the conditions can be used, for example, for 10 to 15 minutes each, in the order listed above, repeating any or all of the steps listed.

Selective hybridization of an oligonucleotide with a methylated DNA sequence can be detected, for example, by using an oligonucleotide that includes a detectable label. The detectable label can be any molecule that conveniently can be linked to the oligonucleotide and detected using readily available equipment. For example, the detectable label can be a fluorescent compound such a Cy3, Cy5, Fam, fluorescein, rhodamine, or a green fluorescent protein or enhanced or modified form thereof; a radionuclide such as sulfur-35, technicium-99, phosphorus-32, tritium or iodine-125; a paramagnetic spin label such as carbon-13, Gd-157, Mn-55, Dy-162, Cr-52, or Fe-56; a luminescent compound such as an aequorin; a chemiluminescent compound; a metal chelate; an enzyme such as luciferase or θ-galactosidase, or a substrate for an enzyme; or a receptor or a ligand for a receptor, for example, biotin. The means for detecting the detectable label will be selected based on the characteristics of the label, as will the means for linking the label to an oligonucleotide (see, for example, Hernanson, "Bioconjugate Techniques" (Academic Press 1996), which is incorporated herein by reference).

Selective hybridization also can be detected, for example, by utilizing the oligonucleotide as a substrate for a primer extension reaction, further contacting the sample with deoxyribonucleotides (dNTPs), including, if desired, a detectable dNTP (e.g., a fluorescently labeled dNTP, a digoxigenin labeled dNTP, or a biotin labeled dNTP), and a DNA dependent DNA polymerase under conditions sufficient for the primer extension reaction to proceed, and detecting a product of the primer extension reaction. Conditions for performing a primer extension reaction are well known in the art (see, for example, Sambrook et al., supra, 1989).

In certain aspects, primer extension is performed with a pair of primers, which are used to amplify the sequence. In one embodiment of the invention, the primers are designed such that they flank a recognition site of the methylation-sensitive restriction enzyme (e.g., HpaII) used to the digest sample DNA according to the invention. Amplified sequences can be detected, for example, by electrophoresis or autoradiography, as an indication of selective hybridization.

Amplification according to the present invention is typically polymerase chain reaction (PCR). However, the skilled artisan will recognize that according to other non-limiting embodiments of the invention, amplification may be performed by other methods known in the art. The invention contemplates that amplification can be performed using any primer-dependent amplification protocol, including but not limited to, Ligase Chain Reaction (LCR) (e.g., Wu & Wallace, 1989, *Genomics* 4:560) and other methods that will be known in the art.

A typical PCR amplification reaction is performed under conditions that allow selective hybridization of the forward and reverse primers of an amplification primer pair to the target nucleic acid molecule. Generally, the reaction is performed in a buffered aqueous solution, at about pH 7-9, usually about pH 8. In addition, the reaction generally is performed in a molar excess of primers to target nucleic acid molecule, for example, at a ratio of about 100:1 primer: captured DNA. Where the amount of the target nucleic acid molecule in a sample is not known, for example, in a diagnostic procedure using a biological sample, a range of primer amounts can be used in samples run in parallel, although generally even the addition of a small amount of primers will result in a sufficient molar excess such that the amplification reaction can proceed.

The conditions generally required for PCR include temperature, salt, cation, pH and related conditions needed for efficient copying of the template DNA. PCR conditions include repeated cycles of heat denaturation (i.e. heating to at least about 95° C.) and incubation at a temperature permitting primer:template hybridization and copying by the amplification enzyme. Heat stable amplification enzymes, which eliminate the need to add enzyme after each denaturation cycle, such as the *Thermus aquaticus*, pwo, or *Thermococcus litoralis* DNA polymerases are commercially available. Information regarding the salt, cation, pH and related factors needed for enzymatic amplification activity are available from commercial manufacturers of amplification enzymes.

The deoxyribonucleoside triphosphates, dATP, dCTP, dGTP, and dTTP, can be added to the synthesis mixture either separately or as a mixture, which can further include the primers, in adequate amounts and the resulting solution is heated to about 90°-100° C. from about 1 to 10 minutes, preferably from 1 to 4 minutes. After this heating period, the solution is allowed to cool to room temperature, which is preferable for the primer hybridization. To the cooled mixture is added an appropriate agent for effecting the primer extension reaction, generally a polymerase, and the reaction is allowed to occur under conditions as disclosed herein (see Example 1) or otherwise known in the art. Where the polymerase is heat stable, it can be added together with the other reagents. The polymerase can be any enzyme useful for directing the synthesis of primer extension products, including, for example, *E. coli* DNA polymerase 1, Klenow fragment of *E. coli* DNA polymerase I, T4 DNA polymerase, other available DNA polymerases, polymerase muteins, reverse transcriptase, and other enzymes, including heat-stable enzymes, as are well known in the art and commercially available.

The methods of the present invention are particularly amenable to quantification of methylated CGIs in DNA from heterogeneous samples. In one embodiment, methylated DNA captured as described above is amplified using a quantitative PCR (QPCR) reaction (e.g. as described in U.S. Pat. Nos. 5,567,583 and 5,348,853), which can be real time Quantitative PCR. The skilled artisan will appreciate that various modifications of the methods will also be suitable for use in accordance with the present invention including Quantitative Competitive Reverse Transcription-PCR [QC(RT)-PCR] or Real Time Detection 5'-Nuclease-PCR(RTDN-PCR; also known as TaqMan RT-PCR).

In general, real-time quantitative PCR is based on the continuous monitoring of a progressive fluorogenic PCR by an optical system. Such PCR systems may use two amplification primers and an additional amplicon-specific, fluorogenic hybridization probe that specifically binds to a site within the amplicon. The probe can include one or more fluorescence label moieties. For example, the probe can be labeled with two fluorescent dyes: 1) a 6-carboxy-fluorescein (FAM), located at the 5'-end, which serves as reporter, and 2) a 6-carboxy-tetramethyl-rhodamine (TAMRA), located at the 3'-end, which serves as a quencher. When amplification occurs, the 5'-3' exonuclease activity of the Taq DNA polymerase cleaves the reporter from the probe during the extension phase, thus releasing it from the quencher. The resulting increase in fluorescence emission of the reporter dye is monitored during the PCR process and represents the number of DNA fragments generated.

Methylation in eukaryotes is variable. The degree of methylation depends not only on the species, but also on the cell type and the developmental stage of the cell. In some mammals, methylation normally is limited to the m5C position of cytosine in the dinucleotide CG, while in plants methylation also occurs at CNG sequences where N is any base (Nelson & McClelland, *Nucleic Acids Res.*, 19 Suppl: 2045-71 (1991).).

Although most CG dinucleotides in mammalian genomes are highly methylated, clusters of stably unmethylated CGs exist throughout the genome. Such clusters of unmethylated CGs are referred to as "CG islands." CG islands have a higher than average G+C content, approximately ten times higher than the rest of the genome, and almost always occur in the 5' region of transcribed DNA (Bickmore & Bird, *Methods Enzymol.*, 216:224-44 (1992).).

CpG islands are unmethylated regions of the genome that are associated with the 5' ends of most house-keeping genes and many regulated genes (Bird, *Nature*, 321:209-213 (1986); Larsen, *Bull. Cancer*, 84:1099-1100 (1997)). The absence of methylation slows CpG decay, and so CpG islands can be detected in DNA sequence as regions in which CpG pairs occur at close to the expected frequency. The fact that CpG islands can be detected in this way indicates that the corresponding germline DNA has been substantially hypomethylated for an extended period of time, and in fact about 80% of CpG islands are common to man and mouse (Antequera et al., *Cell* 62:503-14 (1990); Bird, *Cold Spring Harb. Symp. Quant. Biol.*, 58:281-28 (1993)).

Often CpG islands overlap the promoter and extend about 1000 base pairs downstream into the transcription unit. Identification of potential CpG islands during sequence analysis helps to define the extreme 5' ends of genes, something that is notoriously difficult with cDNA based approaches. Probably because they are associated with genes, CpG islands tend to be unique sequences and are therefore very useful in genome mapping projects.

It is known in the art that a variety of genes are involved in cancer, tumor, metastasis and angiogenesis. Many of these genes have been found to contain regions of DNA hypermethylation in diseased tissues, including cancer. Such hypermethylated genes or proteins encoded by such genes, here included as examples, include but are not limited to: APC, DCC, NF1, NF2, RET, VHL, WT-1, p73, p16, p15, p14, MLH1, MGMT, GSTP1, BRAC, DAP-kinase, e-cadherin, VHL, TIMP4, pax-5, ER, RARb, MDR1, MRP, GSTP1, neuromedin U, Bin1, BRCA-associated protein -1 (BAP-1), JunB, SLF-1, Arginine Deiminase, Her27, Cytoplasmic FMRP interacting protein 2, NKG2E, Apolipoprotein J, ERCC1, TRAIL, DPC4, Apolipoprotein D, Fibronectin, Keratin 14, Transglutaminase, Muc 1, DAZLA, IL-1 R2, Crystallin Alpha2, FLRG, RAD, HNMP-1, BEM45, XAP-5, CLF-1, NKG2E, Dickkoph-1, IGFBP-2, Interferon induced protein 6-16, BPAG1, Inbibin Beta B, W27472, Alpha-1 type XVI collagen, ALP-1, among others. Furthermore, for a majority of these genes, if not for all of these genes, the expression is regulated by methylation and hence also by hypermethylation. Moreover, most of these genes, if not all or these genes, have multiple methylation sites, resulting in a fine-tuning of regulation, but also in aberration of regulation by hypermethylation. In short, a gene may have several methylation sites which may be subject of hypermethylation. These methylation sites may be located in the promoter region, including the regulation region, and methylation sites may also be located in the coding regions, and outside coding regions.

The present invention provides a method for quantifying methylation, particularly hypermethylation, in sequences associated with cancer. As such, the methods of the invention can be used to detect cancer in a human subject. As exemplified below, quantification of specific regions of DNA hypermethylation in a sequence known to be hypermethylated in cancer can be measured with a high degree of specificity and sensitivity using the methods of the invention. The quantity or degree of methylation of a DNA sequence can be expressed as the methylation index (MI) for that sequence. The MI of a DNA sequence is the ratio of the amount of methylated alleles of the sequence to the amount of methylated alleles in a maximally methylated control sample (e.g., one that has been treated with M.SssI.)

In one embodiment of the invention, detection of an MI of at least 3 standard deviations greater than the background for a DNA sequence known to be hypermethylated in cancer is an indication of cancer. In another embodiment, an MI>0.2 is indicative of cancer. The MI value can be expressed numerically or can be displayed as a gray-scale gradient, with white indicating an MI of 0 and black representing an MI of 0.99.

As detailed below, hypermethylation of GSTP1, MDR1, PTGS2 and ESR1 were found to correlate with prostate cancer using the methods of the present invention. Thus, in one embodiment, the present invention provides a method for detecting cancer by detecting in a biological sample from an individual an MI at least 3 standard deviations greater than background for at least one sequence of a GSTP1, a MDR1, a PTGS2 or an ESR1 gene. In another embodiment of the invention, an MI>0.2 for at least one of these sequences is indicative of cancer. In certain aspects, the sequences of a GSTP1, a MDR1, a PTGS2 or an ESR1 gene for which hypermethylation is indicative of prostate cancer, includes sequences amplified by a primer pair selected from SEQ ID NOs:5 and 6; 7 and 8; 9 and 10; or 11 and 12.

The analysis detailed below in the Examples demonstrates that the CGI hypermethylation pattern at GSTP1, PTGS2, and MDR1 detected using the methods of the invention could identify prostate cancer with sensitivities >95% and specificities approaching 100%. Furthermore, the sensitivity, specificity, and dynamic range achieved by COMPARE-MS are highly comparable or even superior to those reported for MSP, MethyLight, and HeavyMethyl.

As detailed below in the Examples, four out of five primary prostate cancer cases in which MethyLight could not detect any GSTP1 CGI hypermethylation were detected by the COMPARE-MS assay. Provocatively, a larger fraction of the tumor-adjacent benign prostate tissues had a small, but significant, amount of methylated CGIs at the GSTP1, PTGS2, and MDR1 genes when analyzed by COMPARE-MS than when analyzed by MethyLight. This finding is in agreement with recent studies showing that the normal epithelia and stroma in tumor-adjacent benign tissues in breast cancers displayed significant hypermethylation of CpG islands (Hu et al., *Nat Genet*, 37, 899-905 (2005). Most of the tumor-adjacent benign tissues examined had some prostatic intraepithelial neoplasia (PIN) and/or proliferative inflammatory atrophy (PIA) lesions, which have been shown to have some methylation at the GSTP1 CGI by MSP, but only after rigorous purification of these cells by laser capture microdissection (LCM) (Nakayama et al., *Am JPathol*, 163:923-933 (2003)). The results described herein for the methods of the present invention, even without LCM, were able to quantitatively detect trace amounts of hypermethylation at these CGIs by COMPARE-MS, illustrating the utility of this technique in highly heterogeneous tissues containing only a small amount of methylated DNA. However, since LCM was not used, the possibility that the detected DNA hypermethylation was due to trace contamination by cancer cells could not be ruled out.

A significant advantage of present invention over previous methods is that it does not require sodium bisulfite modification. This may allow for higher compatibility with high-throughput, automated, micro-titre based platforms, and greater ease in the design of real-time PCR primers since there is no reduction in genome sequence complexity. Also, typically, MSP and MethyLight identify the prevalence of a single pattern of methylation at the CpG dinucleotides interrogated by the primers and probes. Although theoretically it may be possible to carry out multiple reactions, each interrogating a different pattern and different set of CpGs, the low sequence complexity of bisulfite treated DNA limits the application of such strategies. COMPARE-MS, on the other hand, was designed to detect a broader range of abnormal methylation patterns across a large set of CpG dinucleotides without significant design limitations.

Enrichment of methylated DNA by the combination of digestion with HpaII and capture with the MBD2-MBD minimized the rate of false positives, while maintaining exquisite sensitivity. Furthermore, these processes involve minimal "hands-on" time and small reaction volumes, making COMPARE-MS highly compatible with automated, high-throughput, micro-titer plate analysis. After the initial assay development and optimization stages, the methylation pattern of >160 prostate tissue and cell line samples at multiple CGIs could be determined in a single day. Thus, the COMPARE-MS is well suited to high-throughput assay design using e.g., a multi-well format that may be automated, for example by robotics. In addition, multiplexing samples and sequences detected is clearly possible with the COMPARE-MS assay.

The materials for use in the methods of the invention are ideally suited for the preparation of a kit. Such a kit may comprise a carrier means containing one or more container means such as vials, tubes, and the like, each of the container means comprising one of the separate elements to be used in the method. One of the container means may comprise a methylation-sensitive restriction enzyme, while another may contain a capture reagent. Kits may also contain one or more primers or probes which is or can be detectably labeled for the detection of specific methylated sequences. Such primer or probe may be, for example, a nucleic acid sequence specific for a GSTP1 promoter region. In certain embodiments, the kit may also contain a container comprising one or more primer pairs for amplifying hypermethylated DNA sequences. Such primers include, for example, SEQ ID Nos.: 5-18 and combinations thereof.

EXAMPLES

The following examples are intended to illustrate but not to limit the invention in any manner, shape, or form, either explicitly or implicitly. While they are typical of those that might be used, other procedures, methodologies, or techniques known to those skilled in the art may alternatively be used.

Example 1

Materials and Methods

Cell Culture, Tissue Samples, and DNA Isolation

Genomic DNA from LNCaP, PC3, LAPC4, C42B, and CWR22Rv1 prostate cancer cell lines, PrEC normal prostate cells, prostate benign tissues from 13 brain-dead transplant tissue donors with no evidence of prostate disease, primary prostate cancer tissues from 130 men undergoing radical prostatectomy, and tumor-adjacent benign tissues from 12 of these 130 men, were obtained as previously described (Yegnasubramanian, et al., *Cancer Res.*, 64:1975-86. (2004)). DNA quantitation was carried out prior to restriction enzyme digestion and MBD2-MBD capture and was performed by UV absorbance on a standard spectrophotometer and verified by real-time PCR of the Beta-globin gene to ensure that DNA was of ample quality for reliable quantitative PCR amplification. See Bastian et al., supra; Nakayama, et al., *Am. J. Pathol.*, 163:923-33 (2003).

Cloning, Expression, and Purification of MBD2-MBD Polypeptides

To produce recombinant 6His-tagged methyl-binding domain polypeptides from the human MBD2 (MBD2-MBD), MBD2-MBD cDNA sequence was amplified from clone MGC-45084 (American Type Culture Collection), using PCR primers 5'-GGATCCATGGAGAGCGGGAAGAG-GATGGA-3' (SEQ ID NO: 1) and 5'-GAATTCCATCTTTC-CAGTTCTGAAGT-3' (SEQ ID NO:2) containing BamHI and EcoRI recognition sites. A modified pFastBac 1 baculovirus expression vector (Invitrogen), pFBC6H was generated by inserting the sequence 5'-CGCGGCAGCCATCAC-CATCACCATCACTAA-3'(SEQ ID NO:3), which encodes a 6-histidine tag, into pFastBac™ 1 between the EcoRI and XbaI sites. The PCR amplified cDNA sequences were then introduced into pFBC6H after linearization with BamHI and EcoRI. The pFBC6H-MBD2-MBD expression constructs were used to transform DH10Bac™ *E. coli* Competent Cells (Invitrogen) to form MBD expression bacmids via site-specific transposition. The expression bacmids were then transfected into Sf9 insect cells for production of recombinant MBD2-MBD polypeptide encoding baculovirus particles, which were used to infect additional Sf9 cells (1 MOI, 48 hours) to generate recombinant MBD2-MBD proteins containing a C-Terminal 6× histidine tag. Recovery of recombinant 6-His-tagged MBD2-MBD polypeptides was accomplished by methods similar to those described previously (Lee et al., *J Biol. Chem.*, 280:40749-56 (2005)). Briefly, the infected Sf9 cell pellets were resuspended in native binding buffer containing 50 mM NaPO$_4$, 0.5 M NaCl, 10 mM imidazole and 1× Complete EDTA-free Protease Inhibitor cocktail (Roche Diagnostics). Cells were lysed by two freeze-thaw cycles and the DNA was sheared by passing the sample through 20-gauge needles 4 to 6 times. The soluble fraction was mixed with pre-washed Ni-NTA Superflow resin (Qiagen) and incubated at 4° C. for 2 hours with rotation to allow maximum binding. The supernatant, designated as flow-through, was removed after centrifugation for 1 minute at 1,000 rpm. The resin was washed three times with 1× Native Wash Buffer containing 50 mM NaPO$_4$, 0.5 M NaCl, 35 mM imidazole and 1× Complete EDTA-free Protease Inhibitor cocktail. The recombinant proteins were then eluted from the resin with Native Elution Buffer (50 mM NaPO$_4$, 0.5 M NaCl, 250 mM imidazole, protease inhibitor cocktail). The eluates were subjected to buffer exchange using an Amicon® Ultra-15 centrifugal filter device (5000 MWCO, Millipore). The recombinant proteins were stored in buffer containing 20 mM HEPES buffer, 0.1 M KCl, 0.2 mM EDTA, 0.5 mM DTT, 20% glycerol, and 1× Complete EDTA-free Protease Inhibitor cocktail at -80° C. until further use. The final concentration of recombinant MBD2-MBD polypeptide was determined by the BCA assay (Pierce, Rockford, Ill.).

Fluorescence Polarization Analysis of Methyl-Binding Domain Polypeptide Binding to Oligonucleotide Substrates 10 nM of annealed, fluorescently-labeled hairpin oligonucleotides with the sequence 5'-6FAM-ATCGTCG-TACGTTTTCGTACGACGAT-3' (SEQ ID NO:4) with no methylated CpGs (unmethylated hairpin), 2 methylated CpGs at the 2$^{nd}$ and 5$^{th}$ CpGs from the 5' end (1 symmetrically methylated CpG hairpin), 3 methylated CpGs toward the 3' end (3 asymmetrically methylated CpG hairpin), 4 methylated CpGs at the 1$^{st}$, 2$^{nd}$, 5$^{th}$, and 6$^{th}$ CpGs from the 5' end (2 symmetrically methylated CpG hairpin), or 6 methylated CpGs (3 symmetrically methylated CpG hairpin) were incubated with various concentrations of recombinant MBD2-MBD in a 50 μL reaction volume containing 4% glycerol, 1 mM MgCl$_2$, 0.5 mM EDTA, 0.5 mM DTT, 50 mM NaCl, 10 mM Tris-HCl (pH 7.4), 0.2% Tween-20 for 1 hour at room temperature with gentle shaking. Fluorescence polarization measurements were taken in triplicate using a Beckman Coulter DTX 880 Multimode Detector as described previously (Lee et al., (2005), supra). Briefly, fluorescence anisotropies (r) were calculated as $$r=(I_{\parallel}-I_{\perp})/(I_{\parallel}+2I_{\perp})$$

where $I_{\parallel}$ represents the fluorescence intensity parallel to the incident light, $I_{\perp}$ represents the fluorescence intensity perpendicular to the incident light. In order to estimate the EC50, which is defined as the effective protein concentration required for binding 50% of the hairpin oligonucleotides, r was plotted against MBD2-MBD polypeptide concentration, and curve-fitted to a sigmoidal binding curve using SigmaPlot 8.0 (Systat Software, Richmond, Calif.).

COMPARE-MS Assay and Real-Time PCR

An overview of the COMPARE-MS assay is shown in FIG. 1. DNA samples were digested at 37° C. for 3 hours with 15 U AluI (NEB, Beverly, Mass.) with or without 15 U of HpaII (NEB, Beverly, Mass.). After digestion, restriction enzymes were heat inactivated at 65° C. for 30 minutes. 2.5 μL of Protein G Magnetic Beads (NEB, Beverly, Mass.) were gently shaken for 1 hour at room temperature with 1 μg of Penta-His Antibody (Qiagen, Valencia, Calif.), 160 nM MBD2-MBD-6H is, and 200 ng of an unmethylated self-ligated TOPO-TA plasmid (Invitrogen, Carlsbad, Calif.), in 97.5 μL of BW Buffer (4% glycerol, 1 mM MgCl$_2$, 0.5 mM EDTA, 0.5 mM DTT, 50 mM NaCl, 10 mM Tris-HCl (pH 7.4), 0.2% Tween-20, and 1× Complete EDTA-free Protease Inhibitor cocktail. Unbound antibody and MBD polypeptides were removed by immobilizing beads on a Magnetight™ HT96™ magnetic rack (Novagen, San Diego, Calif.) and removing the supernatant. Restriction enzyme digested DNA samples were diluted in 100 μL of BW buffer and then incubated with the beads for 1 hour at room temperature with gentle shaking. The beads were then immobilized on the Magnetight™ HT96™ rack and washed five times with BW Buffer. After the final wash, 20 μL of 1 mM Tris-HCl pH 8.0 was added and the reaction was heated to 95° C. for 15 minutes to elute the DNA. The magnets were again immobilized on the Magnetight™ HT96™ rack and the supernatant containing the released DNA was removed and stored at -20° C. until further use. These DNA samples were then subjected to real-time PCR in 50 μL reaction volumes containing 1×iQ™ SYBR® Green Supermix (Biorad, Hercules, Calif.), and 400 nM forward and reverse primers. Primer sequences for assayed CGIs are shown in Table 1.

TABLE 1

PCR primers used in COMPARE-MS assay

| Gene Symbol | Forward Primer | Reverse Primer |
|---|---|---|
| GSTP1 | 5'-GGGACCCTCCAGAAGAGC-3' (SEQ ID NO: 5) | 5'-ACTCACTGGTGGCGAAGACT-3' (SEQ ID NO: 6) |
| PTGS2 (COX2) | 5'-GGAGAGGAAGCCAAGTGTCC-3' (SEQ ID NO: 7) | 5'-GGTTTCCGCCAGATGTCTTT-3' (SEQ ID NO: 8) |
| MDR1 (ABCB1) | 5'-GTGGGTGGGAGGAAGCAT-3' (SEQ ID NO: 9) | 5'-TCTCCAGCATCTCCACGAAG-3' (SEQ ID NO: 10) |
| ESR1 | 5'-CTCGGGCTGTGCTCTTTTTC-3' (SEQ ID NO: 11) | 5'-CCAGATGCTTTGGTGTGGAG-3' (SEQ ID NO: 12) |
| DAPK1 | 5'-CTTGCAGGGTCCCCATTG-3' (SEQ ID NO: 13) | 5'-GTCCGGCTGTCCTCCTCA-3' (SEQ ID NO: 14) |
| CDH1 | 5'-CAGGTGAACCCTCAGCCAAT-3' (SEQ ID NO: 15) | 5'-CACAGGTGCTTTGCAGTTCC-3' (SEQ ID NO: 16) |

TABLE 1-continued

PCR primers used in COMPARE-MS assay

| Gene Symbol | Forward Primer | Reverse Primer |
|---|---|---|
| LINE1 | 5'CGCAGAAGACGGGTGATTTC-3' (SEQ ID NO: 17) | 5'-CCGTCACCCCTTTCTTTGAC-3' (SEQ ID NO: 18) |

PCR reactions consisted of a 95° C. denaturing step for 10 minutes, followed by 45 cycles of 94° C. for 30 sec, 60° C. for 30 sec with real-time detection, and 72° C. for 30 sec. All assays were carried out in duplicates or triplicates. All real-time PCR amplicons contained at least one HpaII restriction enzyme site. M.SssI (CpG Methylase, NEB) treated male WBC genomic DNA served as a positive control for all CGIs, while untreated male WBC genomic DNA served as a negative control. The completion of the M.SssI methyltransferase reaction was verified by showing that the treated DNA could not be fragmented by HpaII restriction enzyme and that all CpGs at the GSTP1 promoter CGI were methylated by bisulfite genomic sequencing (Clark et al., *Nucleic Acids Res.*, 22:2990-97 (1994)). For prostate cell lines and tissues, methylation levels were normalized to the signal generated by an equal input amount of the positive control to generate a methylation index (MI), which was displayed using a color scale in which red indicates MI>0.99 and white indicates MI=0. Because a quantitative internal control could not be used for each sample, it is important to note that accurate quantitation of DNA in each sample prior to COMPARE-MS analysis is crucial to the accuracy of COMPARE-MS. In this study, DNA quantitation of all samples was performed prior to restriction enzyme digestion and MBD2-MBD capture by UV absorbance and by real-time PCR of the Beta-globin gene. In the few samples in which there was a discrepancy between the absorbance and real-time PCR derived quantities, the real-time PCR quantity was used since this would be a better estimate of amplifiable DNA. As a post-analysis quality check, for specimens that had no detectable signals at all CGIs tested by COMPARE-MS, real-time PCR amplification of LINE1 repetitive elements, which are methylated to a large extent in human genomic DNA, using primers complementary to the LINE1 promoter consensus sequence (GenBank accession X58075), was performed to ensure that recovery of methylated DNA was not compromised during COMPARE-MS.

Bisulfite Genomic Sequencing 500 ng of genomic DNA was bisulfite converted using the EZ DNA methylation Kit™ (Zymo Research, Orange, Calif.) and eluted in 10 µL of TE buffer, pH 7.4. Primers amplifying GSTP1 CpG islands without bias to methylation patterns were: Forward primer, 5'-GTTGGTTTTATGTTGG-GAGTTTTGAGTTTT-3' (SEQ ID NO: 19); Reverse primer, 5'-ATCCTCTTCCTACTATCTATTTACTCCCTAA-3'(SEQ ID NO:20). PCR was carried out in 40 µL reactions containing 1 µL of bisulfite converted DNA, 1× Platinum® Taq buffer (Invitrogen, Carlsbad, Calif.), 1.5 units Platinum® Taq (Invitrogen), 250 µM each dNTPs, 1.5 mM $MgCl_2$, 0.25 µg/µL BSA, 2 µL DMSO, 400 nM Forward primer, 400 nM Reverse primer. Cycling conditions were 95° C. for 3 minutes, 35 cycles of 95° C. for 30 seconds, 50° C. for 30 seconds, and 72° C. for 30 seconds, followed by a 7 minute extension step at 72° C. PCR products were gel purified after electrophoresis on a 1% agarose gel, sub-cloned into pCR®12.1-TOPO® vector (Invitrogen), and analyzed by dideoxy sequencing.

Statistical Analysis

Receiver operator characteristic (ROC) curves were generated using MedCalc (Mariakerke, Belgium) by plotting sensitivity (%) vs. 100-specificity (%) for varying MI thresholds. The 130 primary prostate cancer tissues were defined as true positives while the 13 benign prostate tissues from organ donors were designated true negatives. These curves were used to determine the MI threshold that yields the optimal sensitivity and specificity. Area Under the ROC Curves (AUC) and their 95% confidence intervals were found. The AUC represents the probability that a randomly chosen sample from the true positives group will have an MI that is greater than a randomly chosen sample from the true negatives group. All error bars shown in this study represent s.e.m. COMPARE-MS assay performance linear regression analysis was performed with SigmaPlot 8.0.

Example 2

Figure 2A:
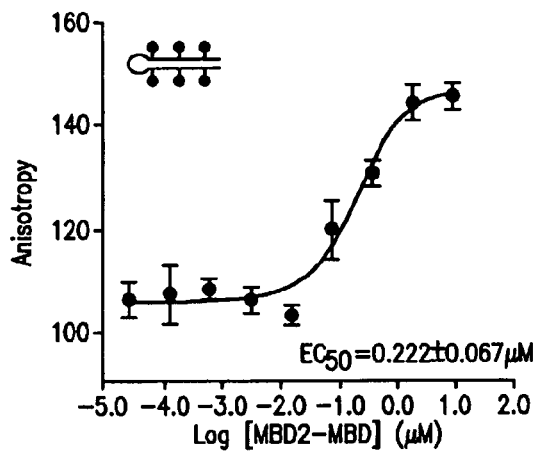
FIG. 2 is a series of graphs showing the determination of MBD2-MBD affinity for symmetrically methylated hairpin olignucleotide ligands. Fluorescence anisotropy measurements were plotted as a function of MBD2-MBD concentration in order to estimate the relative affinity of MBD2-MBD for fluorescently-labeled hairpin oligonucleotides containing three pairs (FIG. 2A), two pairs (FIG. 2B), and one pair (FIG. 2C) of symmetrically methylated CpG dinucleotides. The $EC_{50}$, defined as the MBD2-MBD concentration required to achieve half maximal binding of 10 nM hairpin oligonucleotides, is shown for each case, along with the corresponding s.e.m. Data shown represent mean+s.e.m. for triplicate measurements.
Figure 2B:
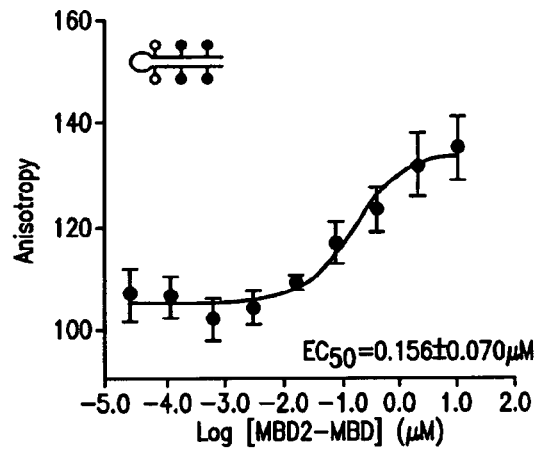
Figure 2C:
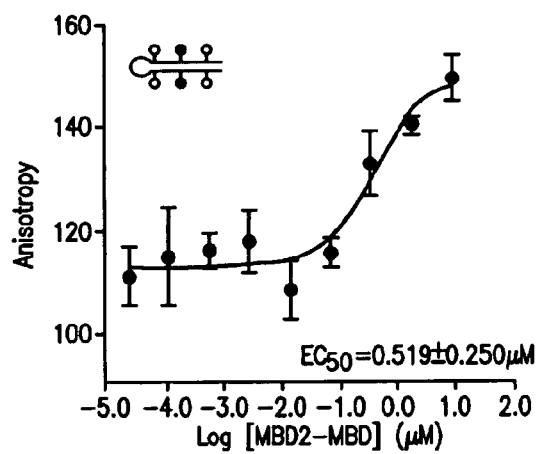

Fluorescence Anisotropy Measurements for Estimation of MBD2-MBD Affinity for Various DNA Templates 6His-tagged methyl-binding domain of human MBD2 (MBD2-MBD) was expressed in Sf9 insect cells using a baculoviral expression system and purified using Ni-NTA Superflow beads (Qiagen, Valencia, Calif.). The affinities of MBD2-MBD for fluorescently labeled hairpin oligonucleotides containing various configurations of CpG methylation were then determined by fluorescence polarization (FIG. 2). The $EC_{50}$ for MBD2-MBD binding to hairpin oligonucleotides containing 2 or 3 symmetrically methylated CpGs was 156 nM and 222 nM respectively (FIGS. 2A and 2B). For hairpin oligonucleotides with a single symmetrically methylated CpG (FIG. 2C) the $EC_{50}$=519 nM. In contrast, the MBD2-MBD did not bind asymmetrically methylated and unmethylated hairpin oligonucleotides to any appreciable extent in the concentration range tested suggesting that the $EC_{50} \gg 10$ µM for these ligands. The high affinity and specificity of MBD2-MBD for symmetrically methylated DNA made it ideal for enrichment and capture of methylated DNA from heterogeneous samples.

Example 3

Dynamic Range of Detection of Methylated GSTP1 CGIs by COMPARE-MS and Each of its Components Individually Digestion with a methylation-sensitive restriction enzyme alone, MBD2-MBD capture of methylated DNA alone, and the combination of the two approaches were compared for the ability to distinguish between methylated and unmethylated GSTP1 promoter CGIs (FIG. 3). Genomic DNA containing completely methylated GSTP1 promoter CGIs was generated by treating WBC genomic DNA, which is normally unmethylated at this CGI, with M.SssI DNA methyltransferase. In an ideal methylation assay, 100% of the M.SssI treated DNA would be detected while the amount of falsely detected untreated WBC DNA would diminish to zero. For this scenario, the dynamic range, defined as the amount of methylated alleles detected in the M.SssI treated DNA divided by the amount falsely detected in the untreated WBC DNA, would approach infinity.

Figure 3A:
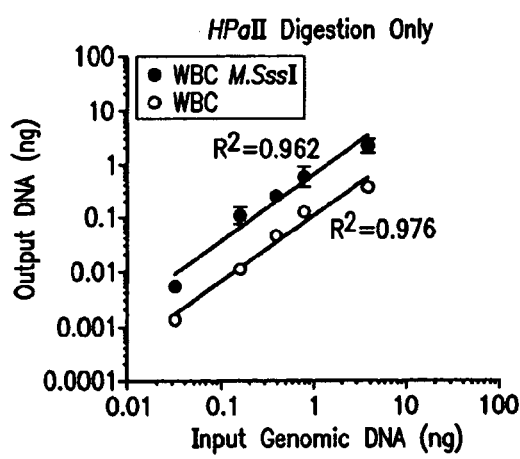
(FIGS. 3A and 3B are plots showing the measured amount of methylated GSTP1 CGIs in M.SssI treated and untreated WBC genomic DNA vs. the amount of input DNA after enriching for methylated DNA by: methylation-sensitive restriction enzymes alone (FIG. 3A), or MBD2-MBD capture alone (FIG. 3B).
Figure 3D:
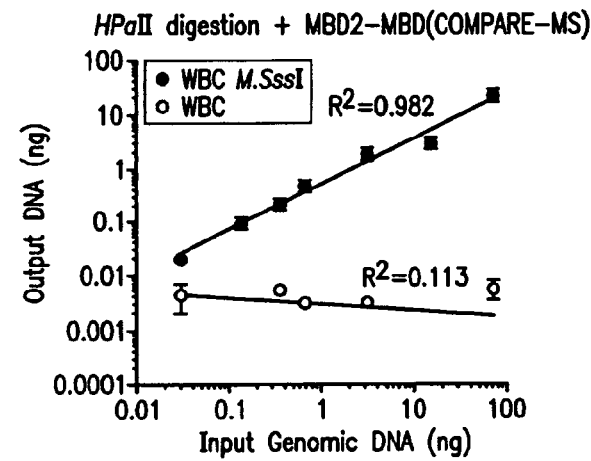
FIG. 3D shows the measured amount of methylated GSTP1 CGIs in M.SssI treated and untreated WBC genomic DNA vs. the amount of input DNA after enriching for methylated DNA by the combination of methylation-sensitive restriction enzyme digestion and MBD2-MBD capture (COMPARE-MS) followed by real-time PCR. When 20-100 ng of input DNA are used, COMPARE-MS has a >5000 fold dynamic range, which is of ~500 fold higher than that of methylation-sensitive restriction enzyme used alone and ~5-10 fold higher than that of MBD2-MBD capture used alone.
Figure 3B:
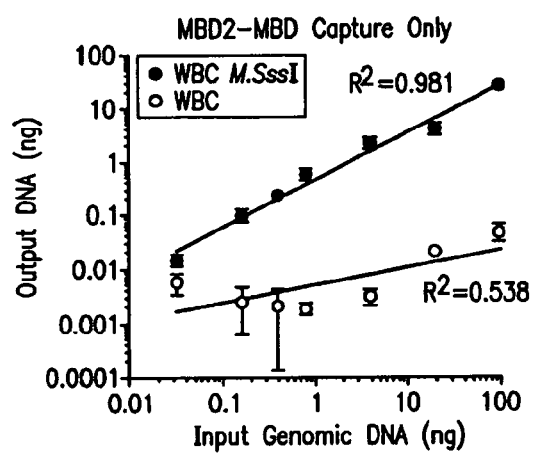

HpaII restriction enzyme digestion followed by real-time PCR with primers flanking a single recognition site achieved a dynamic range of approximately 6-10 fold at all concentrations of input DNA tested (FIG. 3A). This data is in agreement with a previous study showing a dynamic range of approximately 10 fold when the amplicon contained one HpaII recognition sequence. (Singer-Sam et al., *Nucleic Acids Res.*, 18:687 (1990)). MBD2-MBD capture of methylated DNA alone followed by real-time PCR showed a maximum dynamic range of approximately 500-700 fold at high (4-100 ng) input DNA amounts steadily decreasing to a minimum dynamic range of approximately 3-10 fold at low (32 pg) input DNA amounts (FIG. 3B). At high concentrations of input DNA, a small amount of untreated WBC DNA was detected above background, but this was likely due to non-specific binding of the unmethylated DNA to the beads as opposed to specific binding of unmethylated DNA to the MBD2-MBD, since the same amount of background DNA capture occurred even in the absence of MBD2-MBD (FIG. 3C). When input DNA was first cut with HpaII, then captured with the MBD2-MBD, and finally subjected to real-time PCR, the maximum dynamic range was approximately 5,000-10000 fold with 20-100 ng input DNA, decreasing to 10 fold at 32 pg (5-6 genomic equivalents) input DNA (FIG. 3D). Therefore, the combination of these techniques, termed COMPARE-MS, is superior to either technique used alone. Furthermore, the ability to detect hypermethylated GSTP1 CGIs was highly linear ($R^2=0.982$) over a 3,125 fold range of input DNA. In contrast, the signals from unmethylated DNA templates were uniformly low and unrelated to input DNA amount ($R^2=0.113$), suggesting that these low signals were due to the random noise in the assay, likely resulting from carrying out high cycle numbers in real-time PCR.

The COMPARE-MS assay allowed reliable quantitation of methylated CGIs even when only 0.03% or 1/3,125 of input alleles were methylated. This sensitivity and specificity would allow accurate detection of hypermethylated cancer DNA in >1,000 fold excess unmethylated normal DNA, as would be found in heterogeneous DNA samples obtained from non-dissected tissues, biopsy specimens, and bodily fluids.

Example 4

COMPARE-MS Assay Performance in Simulated Heterogeneous Samples

Figure 3E:
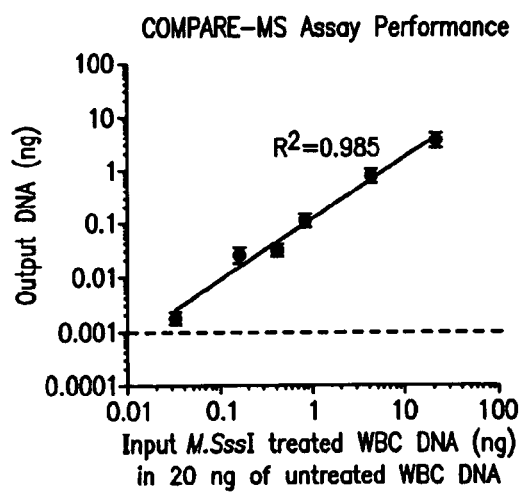
FIG. 3E is a plot showing measured output methylated GSTP1 CGIs as determined by COMPARE-MS when decreasing amounts of M.SssI treated WBC DNA is diluted in 20 ng of untreated WBC genomic DNA. The dashed line is a reference representing the mean COMPARE-MS output (0.0065±0.0023 ng) when 4 identical replicates of 100 ng of untreated, unmixed WBC genomic DNA were analyzed. COMPARE-MS performance in this series of simulated heterogeneous samples, as shown in FIG. 3E, is highly linear for almost four orders of magnitude and nearly identical to that seen with homogeneously methylated samples as shown in FIG. 3D, showing robust reproducibility and sensitivity. Data in FIGS. 3A-E) represent mean±s.e.m. for triplicate measurements.
Figure 3C:
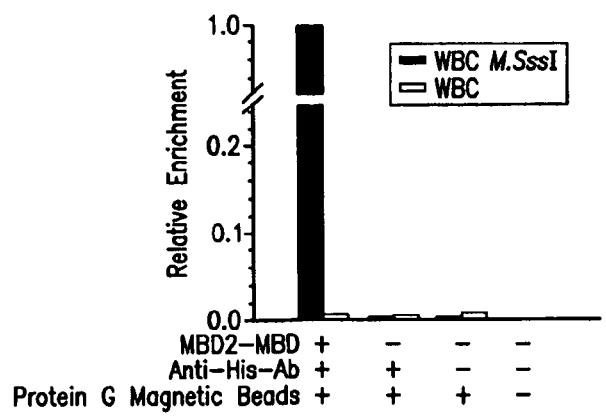
FIG. 3C shows a plot of relative enrichment of M.SssI treated or untreated WBC DNA with or without MBD2-MBD, anti-His antibody, and protein G magnetic beads. The degree of capture of unmethylated DNA (untreated WBC DNA) in the presence of MBD2-MBD is less than or equal to the capture of DNA in the absence of MBD2-MBD or anti-His antibody, showing that capture of unmethylated DNA during the DNA capture step of COMPARE-MS is almost completely due to low amounts of non-specific binding to the protein G magnetic beads, as opposed to low-level binding of the MBD2-MBD to unmethylated DNA.

To test the potential of the assay more directly, we examined the COMPARE-MS assay's performance by using it to analyze samples containing decreasing amounts (20 ng-32 pg) of M.SssI treated WBC genomic DNA diluted in a fixed amount (20 ng) of untreated WBC DNA (FIG. 3E). These mixtures were a simulation of heterogeneous samples. A fixed amount of 20 ng of untreated WBC genomic DNA was used because this represented a realistic amount that would be desirable to input in actual clinical or research assays in order to conserve DNA specimens. As anticipated by the dynamic range studies, the COMPARE-MS assay had a linear quantitative response ($R^2=0.985$) over a broad dilution range spanning more than three orders of magnitude. Furthermore, the assay performance in samples diluted in excess unmethylated DNA was extremely similar to the performance in samples containing pure methylated DNA (FIGS. 3D-3E). The COMPARE-MS assay could reliably detect 32 pg (5-6 cells) of methylated DNA without being overwhelmed by the 625 fold excess of unmethylated genomic DNA. The same reliability in quantitation was achieved when 32 pg of methylated DNA was diluted in 100 ng (~3125 fold) of excess unmethylated DNA, confirming that accurate quantitation of GSTP1 CGI hypermethylation could be achieved in mixtures containing 625-3,125 fold excess contaminating unmethylated DNA.

Example 5

CGI Hypermethylation Profile of Prostate Cancer Cell Lines by COMPARE-MS

COMPARE-MS was used to assess the quantity of hypermethylated CGI sequences at 6 cancer-related genes in 6 prostate cancer cell lines and normal prostate epithelial cells (PrECs) in primary culture (FIG. 4). CGI sequences at GSTP1, PTGS2 and MDR1 were found to be frequently and prevalently methylated in multiple prostate cancer cell lines. The ESR1 CGI was highly methylated in PC-3 cells, slightly methylated in the DU-145 cells, but unmethylated in the other cell lines. The CGI at DAPK1 was methylated to a small extent in the PC-3 cell line. The CDH1 CGI was not methylated at any of the prostate cancer cell lines. PrECs and WBCs were not methylated at any of the CGIs tested. These experiments demonstrate the general applicability of the COMPARE-MS assay to CGIs at multiple genes (FIG. 4A). With few exceptions, the CGI methylation pattern in these cells determined by COMPARE-MS is extremely similar to the pattern determined by MethyLight (FIGS. 4A-4B) in a previous study. (Yegnasubramanian et al., *Cancer Res*, 64:1975-86 (2004)). Among the exceptions, the MethyLight study did not detect any GSTP1 CGI hypermethylation in CWR22Rv1, while COMPARE-MS detected a significant amount of methylated GSTP1 CGI alleles in this cell line. To test the accuracy of the COMPARE-MS assay, bisulfite genomic sequencing of the GSTP1 CGI in DNA from CWR22RV1, LNCaP and PrEC cells was performed (FIG. 4C). This analysis showed that COMPARE-MS was accurate in predicting a high degree of GSTP1 CGI hypermethylation in the CWR22Rv1 cell line (MI=0.71). As seen by the bisulfite sequencing data, the reason that MethyLight could not detect any GSTP1 CGI hypermethylation in this sample is most likely that many of the CpGs interrogated by the MethyLight primers and probe were unmethylated in almost all of the alleles. However, the ability of the COMPARE-MS assay to correctly detect a high degree of hypermethylation at the CWR22Rv1 was somewhat fortuitous since the HpaII site interrogated by the COMPARE-MS assay was highly methylated in this cell line. For instance, when using a different set of real-time PCR primers that flank a single SmaI site at the $11^{th}$ CpG upstream of the −266 position of the GSTP1 promoter (indicated in FIG. 4C), the COMPARE-MS assay detected a very low (MI=0.031), but greater than background degree of hypermethylation. Additionally, when WBC DNA was partially methylated by M.HhaI and M.HpaII at 9 CpG sites (24% of all CpG sites) within the AluI fragment interrogated by the COMPARE-MS assay, only a small, but greater than background, fraction of input alleles was detected (MI=0.036), compared to an equivalent input amount of M.SssI methylated WBC DNA. Therefore, the dynamic range and diagnostic sensitivity of COMPARE-MS would be limited if the CpGs interrogated by the methylation-sensitive restriction enzyme were highly undermethylated compared to the surrounding CpGs or where there is a low density of methylation in the interrogated AluI fragment. This limitation is not unlike that for MSP and MethyLight when the CpGs interrogated by the methylation-specific primers and probes are undermethylated compared to the surrounding CpGs or when there is a low density of methylation at the interrogated CpGs.

Example 6

Figure 6:
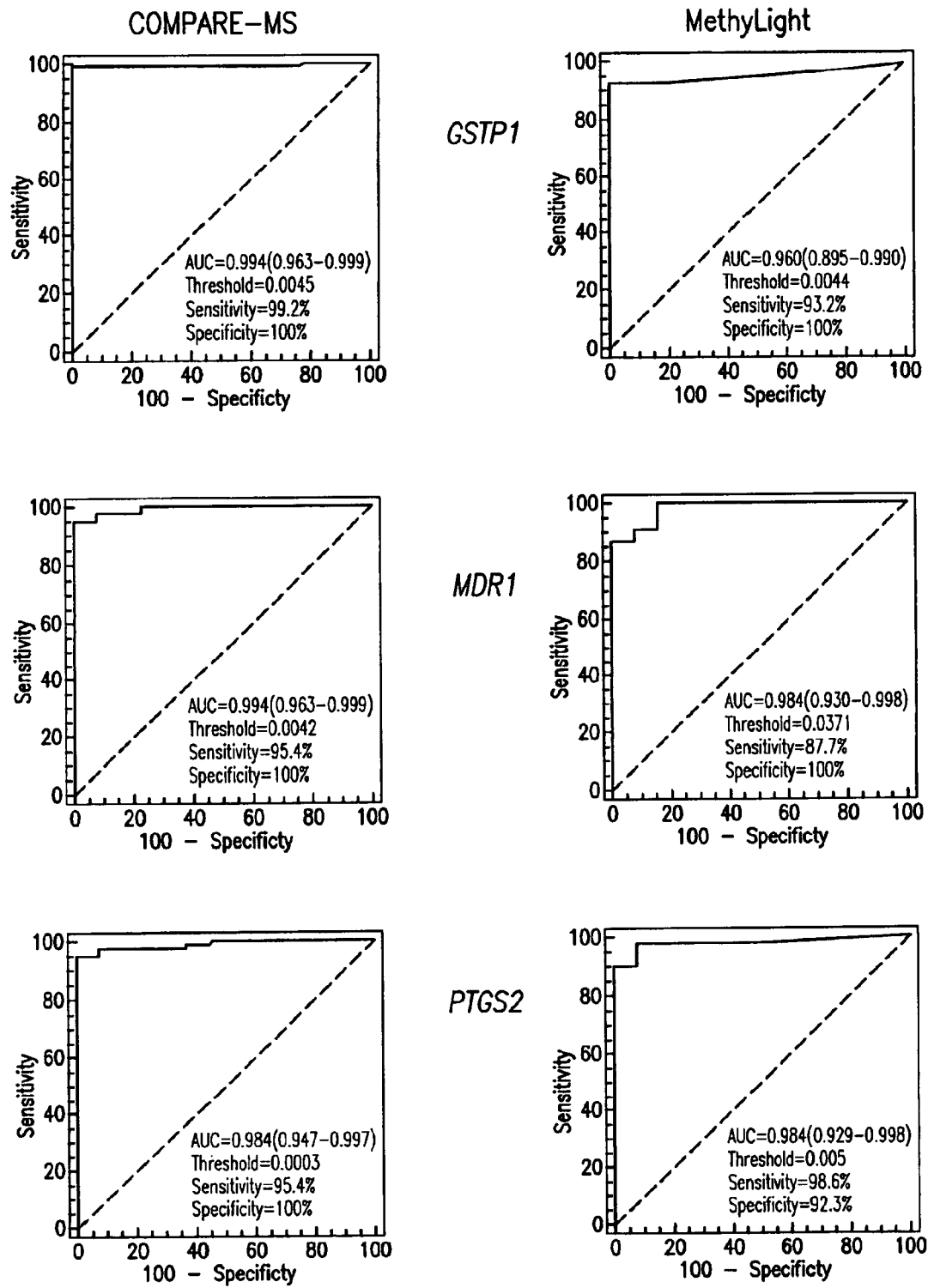
FIG. 6 is a comparison of receiver operator characteristic (ROC) curves obtained by COMPARE-MS with those obtained by MethyLight. ROC curves for hypermethylation at the GSTP1, MDR1, and PTGS2 CGIs in distinguishing between benign and malignant prostate as determined by COMPARE-MS were comparable to those generated by MethyLight (33). An ideal assay would perfectly distinguish between true positives and true negatives and would have an area under the ROC curve of 1.0. The dashed lines represent the ROC curve for a hypothetical test that cannot distinguish between these two groups, giving an AUC of 0.5. CGI hypermethylation at the GSTP1, MDR1, and PTGS2 genes as determined by COMPARE-MS distinguish benign prostate from prostate cancer with high sensitivity and specificity, with AUCs extremely close to the ideal case.

Detection of CGI Hypermethylation by COMPARE-MS in Prostate Cancer and Benign Prostate Tissues To test performance on heterogeneous human tissues, the COMPARE-MS assay was used to determine the extent of methylation at the GSTP1, PTGS2, MDR1, and ESR1 CGIs in benign prostate tissues from 13 transplant organ donors, prostate cancer tissues from 130 men undergoing radical prostatectomy for treatment of localized prostate cancer, and tumor-adjacent benign prostate cancer tissues microdissected from 12 of the 130 men undergoing radical prostatectomy (FIG. 5). Tissues were chosen such that a large subset of the prostate cancer tissues analyzed in this study had been analyzed by MethyLight previously (33). Like the prostate cancer cell lines, the CGIs at GSTP1 (99.2%), MDR1 (95.4%), and PTGS2 (95.4%) were hypermethylated in a large percentage of the 130 primary prostate cancer specimens and had, on average, a high prevalence of methylated copies (mean and median MI>0.15). The ESR1 CGI was methylated in 47.7% of the primary prostate cancers with a low, but above-threshold, prevalence (mean and median MI<0.03). In contrast, benign prostate tissues from organ donors, who did not have evidence of prostatic, malignancies, had undetectable methylation at these CGIs. Interestingly, many of the tumor-adjacent benign tissues exhibited a low (mean and median MI<0.02), but above-threshold, amount of CGI hypermethylation at the GSTP1, MDR1 and PTGS2 genes (frequency of 58.3%, 25%, and 50% respectively). A much smaller percentage of these tissues had detectable CGI hypermethylation by the MethyLight assay (Yegnasubramanian et al., *Cancer Res,* 64:1975-86 (2004)). Receiver operator characteristic (ROC) curves were used to analyze the optimal sensitivity and specificity of GSTP1, MDR1, and PTGS2 CGI hypermethylation as determined by the COMPARE-MS assay in differentiating primary prostate cancer from benign prostate (FIG. 6). Hypermethylation of all three of these CGIs could achieve sensitivities >95% and specificities approaching 100%. The areas under the ROC curves (AUC) for these CGIs as determined by COMPARE-MS approached 1.0 and were comparable to those determined by MethyLight (Yegnasubramanian et al. *Cancer Res,* 64:1975-86 (2004)). Interestingly, four out of the five prostate cancer cases that had undetectable GSTP1 CGI hypermethylation by MethyLight were found to be hypermethylated by the COMPARE-MS assay. Furthermore, the one prostate cancer case that had undetectable GSTP1 CGI hypermethylation by the COMPARE-MS assay was also undetectable by MethyLight. Taken together, these data demonstrate the applicability of the COMPARE-MS assay for the sensitive, specific, and rapid identification of aberrant CGI hypermethylation in heterogeneous tissues.

---

What is claimed is:

1. A method for enriching methylated DNA in a sample comprising:
   a) digesting the sample with a methylation-sensitive restriction endonuclease, wherein the sample comprises methylated DNA, thereby generating methylated DNA fragments;
   wherein the sample comprises less than about 100 ng of DNA;
   b) capturing at least one methylated DNA fragment generated in step a), thereby enriching for methylated DNA.

2. The method of claim 1, wherein the methylated DNA comprises CpG island methylation.

3. The method of claim 2, wherein the methylation sensitive restriction endonuclease is HpaII.

4. The method of claim 1, wherein step a) further comprises digesting the sample with a second restriction endonuclease.

5. The method of claim 4, wherein the second restriction endonuclease is AluI.

6. The method of claim 1, wherein capturing comprises:
   i) contacting the methylated DNA fragments of step a) with a capture reagent that binds methylated DNA, and
   ii) separating bound DNA from unbound DNA.

7. The method of claim 6, wherein the capture reagent is selected from: a methylated-CpG binding domain (MBD) polypeptide and an anti-5-methylcytosine antibody.

8. The method of claim 7, wherein the MBD polypeptide is MBD2.

9. The method of claim 6, wherein the capture reagent comprises a portion of MBD2 comprising the MBD domain.

10. The method of claim 6, wherein the capture reagent is bound to a solid support.

11. The method of claim 10, wherein the capture reagent is attached to the solid support through a his tag.

12. The method of claim 11, wherein the solid support is selected from a bead, a resin, a microtiter plate, a chip, or a test tube.

13. The method of claim 12, wherein the solid support is a magnetic bead.

14. The method of claim 1, further comprising eluting the captured DNA.

15. A method for identifying a methylated DNA sequence comprising:
   a) digesting a sample comprising the methylated DNA sequence with a methylation-sensitive restriction endonuclease, thereby generating methylated DNA fragments;
   wherein the sample comprises less than about 100 ng of DNA;
   b) capturing at least one methylated DNA fragment generated in step a), wherein the captured fragment comprises the methylated DNA sequence;
   c) contacting the methylated DNA fragment captured in step b) with a reagent that identifies the fragment, thereby identifying the methylated DNA sequence.

16. The method of claim 15, wherein the reagent comprises at least one oligonucleotide that selectively hybridizes to the methylated DNA sequence.

17. The method of claim 16, wherein the at least one oligonucleotide is a probe, extension primer or an amplification primer pair.

18. The method of claim 17, further comprising amplifying the methylated DNA sequence with the amplification primer pair.

19. The method of claim 18, wherein amplifying comprises polymerase chain reaction.

20. A method for quantifying a methylated DNA sequence comprising:
a) digesting a sample comprising the methylated DNA sequence with a methylation-sensitive restriction endonuclease, thereby generating methylated DNA fragments;
wherein the sample comprises less than about 100 ng of DNA;
b) capturing the methylated DNA fragments generated in step a), wherein the captured fragments comprise the methylated DNA sequence;
c) contacting the methylated DNA fragment captured in step b) with a reagent that quantifies the methylated DNA sequence.

21. The method of claim 20, wherein the reagent comprises at least one oligonucleotide that selectively hybridizes to the methylated DNA sequence.

22. The method of claim 21, wherein the at least one oligonucleotide is an amplification primer pair.

23. The method of claim 22, comprising quantitatively amplifying the methylated DNA fragment with the primer pair.

24. The method of claim 23, wherein quantitatively amplifying comprises real time quantitative polymerase chain reaction (QPCR).

25. The method of claim 20, wherein the sample comprises at least about 20 ng of DNA.

26. The method of claim 20 wherein an excess of at least about 500 fold excess unmethylated DNA is present in the sample.

27. The method of claim 20 wherein an excess of at least about 1000 fold excess unmethylated DNA is present in the sample.

28. The method of claim 20 wherein an excess of at least about 3000 fold excess unmethylated DNA is present in the sample.

29. The method of claim 20, wherein at least about 30 pg of the methylated DNA sequence is present in the sample.

30. The method of claim 20, further comprising detecting at least one additional methylated DNA sequence in the sample.

31. The method of claim 30, wherein at least about 5 methylated DNA sequences are detected.

32. The method of claim 20, wherein the method comprises a multiplex assay.

33. The method of claim 20, wherein at least about 10 different samples are analyzed.

34. A method for detecting prostate cancer in a subject comprising:
a) digesting a sample from the subject comprising hypermethylated DNA sequences, with a methylation-sensitive restriction endonuclease, wherein hypermethylation of the DNA sequence is indicative of cancer, thereby generating methylated DNA fragments;
wherein the hypermethylated DNA sequences comprise GSTP1, MDR1, ESR1 and PTGS2;
b) capturing the methylated DNA fragments generated in step a), wherein the captured fragments comprise the hypermethylated DNA sequences;
c) contacting the methylated DNA fragments captured in step b) with a reagent that detects the hypermethylated DNA sequences, thereby detecting cancer;
d) quantifying the hypermethylated DNA sequences; and
e) calculating a methylation index of the hypermethylated DNA sequences in the sample.

35. The method of claim 34, wherein the reagent is a primer pair that selectively hybridizes to and amplifies the hypermethylated DNA sequence.

36. The method of claim 35, wherein the primer pair is selected from SEQ ID NOS: 5 and 6, SEQ ID NOS: 7 and 8, SEQ ID NOS: 9 and 10, and SEQ ID NOS: 11 and 12.

37. The method of claim 34, wherein the methylation index is at least three standard deviations greater than the background.

38. The method according to claim 34, wherein the methylation index is >0.2.

39. The method according to claim 34, wherein quantifying comprises quantitatively amplifying the hypermethylated DNA sequences.

40. The method according to claim 39, wherein quantitatively amplifying the hypermethylated DNA sequences comprises quantitative polymerase chain reaction (QPCR).

41. A kit for quantifying a hypermethylated DNA sequence comprising:
a first container containing a methylation-sensitive restriction endonuclease;
a second container containing a MBD capture reagent;
a pair of primers for amplification of the hypermethylated DNA sequence; and
a control DNA sample comprising the hypermethylated DNA sequence treated with M.SssI.

42. A kit for detection prostate cancer comprising:
a first container containing a methylation-sensitive restriction endonuclease;
a second container containing a MBD capture reagent;
at least one pair of primers for amplification of a DNA sequence that is hypermethylated in prostate cancer; and
at least one control DNA sample comprising the hypermethylated DNA sequence treated with M.SssI.

43. The kit of claim 42, wherein the DNA sequence that is hypermethylated in prostate cancer is selected from a sequence of GSTP1, MDR1, ESR1 or PTGS2.

* * * * *